United States Patent [19]
Snell

[11] Patent Number: 5,716,382
[45] Date of Patent: Feb. 10, 1998

[54] PROGRAMMER FOR AN IMPLANTABLE CARDIAC STIMULATING DEVICE

[75] Inventor: Jeffery D. Snell, Oak Park, Calif.

[73] Assignee: Pacesetter, Inc., Sylmar, Calif.

[21] Appl. No.: 510,365

[22] Filed: Aug. 2, 1995

[51] Int. Cl.$^6$ ............................................. A61N 1/362
[52] U.S. Cl. ................................................... 607/30
[58] Field of Search ............................ 607/30, 59

[56] References Cited

U.S. PATENT DOCUMENTS

| | | | |
|---|---|---|---|
| 4,305,397 | 12/1981 | Weisbrod et al. | 607/30 |
| 4,596,255 | 6/1986 | Snell et al. | 128/697 |
| 4,791,936 | 12/1988 | Snell et al. | 128/697 |
| 4,809,697 | 3/1989 | Causey, III et al. | 128/419 PT |
| 4,867,162 | 9/1989 | Schaldach | 607/30 |

OTHER PUBLICATIONS

Garber, Gary R. M.D., et al., "Decision Analysis for Choosing the Hemodynamically Optimum Pacemaker", *Journal of Electrophysiology*, vol. 3, No. 3, pp. 217–220 (1989).

Bernstein, Alan D., et al., "Computer-Assisted Mode Selection in Antibradyarrhythmia Pacing", Presented at the 39th Annual Scientific Session of the American College of Cardiology, New Orleans, Louisiana (Mar. 19, 1990).

Garber, G.R., et al., "A Rule Based Expert System to Choose the Optimal Pacing Mode", Presented at the 4th European Symposium on Cardiac Pacing, Stockholm, Sweden (May 28-31, 1989).

*Primary Examiner*—William E. Kamm

[57] ABSTRACT

This invention provides a therapy decision support system and method for guiding physicians and medical technicians in optimizing a set of adjustable parameters that define the operating characteristics of implantable cardiac stimulating devices. The invention also provides an implantable cardiac stimulating device programmer which can furnish therapy decision support as well as telemetric data retrieval and telemetric programming capabilities.

22 Claims, 6 Drawing Sheets

PROGRAMMER FOR AN IMPLANTABLE CARDIAC STIMULATING DEVICE

BACKGROUND OF THE INVENTION

This invention relates to implantable cardiac stimulating devices, and in particular to a programing system for implantable cardiac stimulating devices. More particularly, this invention provides a therapy decision support system and method that allows physicians and clinical technicians to optimize a set of adjustable parameters that define the operating characteristics of implantable cardiac stimulating devices.

Implantable cardiac stimulating devices are designed to treat cardiac pathologies known collectively as arrhythmias. The term "arrhythmia" refers to the failure of cardiac tissue to contract and relax in a regular, rhythmic fashion. There are two variables that generally define an arrythmia—heart rate and heart beat regularity. For example, if a heart beats at a regular but slower than normal rate, the arrhythmia is referred to as "bradycardia". A regular but faster than normal heart rate is referred to as "tachycardia". Finally, chaotic cardiac activity is known as "fibrillation".

The purpose of an implantable cardiac stimulating device is to detect and terminate cardiac arrhythmias in a patient. Typically, this is accomplished by monitoring cardiac activity (e.g., the intracardiac electrogram, or "IEGM") of a patient through various sensors, and by delivering therapeutic electrical stimulation whenever an arrhythmia is detected. As different arrhythmias require different forms of therapy, historically, different classes of implantable devices have been used to treat them. Thus, "pacemakers" generally deliver low energy pulses for treating bradycardia, "cardioverters" deliver stronger pulses for reverting tachycardia, and "defibrillators" deliver very strong pulses or "shocks" for terminating fibrillation. Modern devices may be capable of providing "tiered therapy," in which the type of electrical stimulation supplied by the device is determined according to the severity of the arrythmia, with more aggressive therapy being applied in response to the more severe arrhythmias. For example, a modern device may serve as a pacemaker and a cardioverter/defibrillator, which is to say, that it can provide therapy for bradycardia, tachycardia and fibrillations.

As medical science and technology progress, treatments for cardiac arrhythmias, and the implantable devices used for their delivery, have become more specific and more sophisticated. Typically, a set of adjustable parameters in the device is programmed to modify the delivered therapy according to the instructions of a physician. These may include parameters that adjust detection mode and detection criteria of the device—for example, parameters that define bradycardia, tachycardia and fibrillation according to rate and regularity, or parameters that determine whether the device sensors act in one or two chambers of the heart (i.e. single- or dual-chamber sensing).

Other adjustable parameters determine the pacing mode or the specifications of the therapy that the device would deliver in response to any particular arrythmia that is detected. For example, a device can be programmed to deliver pacing pulses in one or two chambers of the heart (i.e. single- or dual-chamber pacing), with or without modulation of the pacing rate according to the detected heartbeat.

Parameters that relate to routine or house-keeping functions of the device can also be programmed according to the instructions of a physician. For example, the device can be programmed to record the history of a particular episode of arrhythmia, such as the date and time of detection, heart rate at the time of detection, and result of the therapy. Various other sensor and memory storage units within the device can also be enabled or disabled to enhance the performance of the device and battery longevity, as deemed appropriate by the physician.

Obviously, the greater the number of adjustable parameters, the greater the chance of satisfying particular therapeutic needs of each patient by tailoring those parameters. But there is also greater complexity and more room for confusion in deciding what the appropriate settings should be. Incorrect programming of the device, or presence of two or more conflicting parameter settings may lead to device malfunction. It may, for example, cause delivery of unnecessary or inappropriate pulses—a phenomenon that is categorized as "pacemaker syndrome".

Thus, an immense burden is placed on the physician or the medical technician who must determine the appropriate settings. To make reliable decisions, a physician would need familiarity with vast volumes of information. Not only must physicians keep abreast of the literature and the latest medical advances in the field, they must also understand the complexities of various intricate implantable devices. With new and more sophisticated devices from different manufacturers entering the market at an increasingly rapid pace, this task is becoming more formidable every day.

In spite of some recent attempts in the art to lighten the burden of the therapy decision-making process, known systems generally have not advanced beyond recommending an optimum pacing mode for implantable pacemakers. For example, Bernstein and Parsonnet have described a computer implementation of an algorithm that calculates a pacing mode based on 11 pieces of encoded data entered by the operating physician (presented at the "39th Annual Science Session of the American College of Cardiology," New Orleans, La.—March 1990). Similarly, Garber et al. has programmed an algorithm on a personal computer that can determine an optimum pacing mode following a question-and-answer session with the physician (J. Electrophys. (1989) 3, 217–220).

Simply recommending a pacing mode, however, is unsatisfactory. It can leave the physician unaware of why a particular mode was recommended, what alternatives are available, or how to set the other adjustable parameters on the implantable device. Furthermore, as mentioned previously, in many cases two settings may interfere with each other's function and such a conflict may easily escape the physician's notice. The recommendations made by the prior art systems are also restricted to only one type of implantable cardiac stimulating device whereas a physician must typically deal with many different devices from various manufacturers.

Therefore, it would be desirable if a decision support system could present the physician with a list of a multitude of available parameters that can be adjusted in an implantable device, and if it could make setting recommendations on any of those parameters according to the physician's choice. Furthermore, it would be desirable if the system could identify possible conflicts among parameter settings and warn the physician accordingly. It would also be desirable if the decision support system presented literature citations or scientific data and reasoning explaining why a particular mode or a specific parameter setting was recommended. To expand the utility of a decision support system it would also be desirable if the decision support system had the flexibility to recognize various types and models of implantable cardiac stimulating devices and make recommendations accordingly.

Another shortcoming of the known computer-based systems is that they require the physician to perform various tasks on a number of different machines or instruments before programming an implantable device. For example, to provide a properly programmed device for a new patient, a physician first has to obtain a large amount of data regarding the patient's medical condition, possibly from a central hospital database, and then enter this data into the computer (e.g., a "personal computer") on which the system is operating. Next, the physician must provide the system with the specifications of the implantable device and the present settings of the adjustable parameters in the device. This information is typically available through apparatus known as a "device programmer," which can communicate with the implantable device telemetrically. Once the system is provided with all the necessary information, it can recommend a pacing mode. The physician must then go back to the device programmer, and adjust the implantable device parameters telemetrically. Having now programmed the device, the physician would have to return to the patient file or database and make a record of the settings for future reference.

Clearly, this mode of operation is cumbersome, inefficient and overly time-consuming. Therefore, a decision support system that could gather some or all of the relevant data automatically would be desirable. It would also be desirable if the same decision support system could arrive at optimal settings for device parameters after gathering the data, and if the same system could automatically program the implantable device according to the instructions of the physician.

SUMMARY OF THE INVENTION

In accordance with the present invention, a decision support system is provided that can generate recommendations for programming of implantable cardiac stimulating devices, according to rules from one or more rule sets that define the operations of various cardiac stimulating devices. Rule sets are selected based on the type of the implantable cardiac stimulating device to be programmed. The system utilizes a rule engine unit that engages an operator in an interactive question and answer session according to the rules of the selected rule set. Based on the information acquired from the operator, the rule engine determines an appropriate operating condition for the implantable cardiac stimulating device or a plurality of operating conditions from which the physician can choose. The system then displays the operating condition as a programming recommendation to the operator.

Preferably, the rule sets provide the operator with a list of adjustable parameters in an implantable device so that programming recommendations regarding any of a number of adjustable parameters in an implantable device can be obtained from the same decision support system.

The present invention also provides a decision support system which utilizes a patient/device database unit for storage of medical information of patients and operating parameters for various implantable cardiac stimulating devices. The patient/device database can also serve as a means for storage of the rule sets. The decision support system can thus retrieve some or all of the information required for generating a recommendation directly from the patient/device database and arrive at a programming recommendation.

Therefore, in accordance with the present invention a method for arriving at recommendations for programming of implantable cardiac stimulating devices is provided. The method involves selection of an appropriate rule set from a set of available rule sets according to information acquired from an operator or from a patient/device database. The operator is then engaged in a question and answer session wherein questions are posed according to the rules of the selected rule set and the operator's answers to previous questions. In this way, the operator goes through the rule set and upon completion of the session is presented with programming recommendations. Preferably, each recommendation is accompanied by comments, or citations from the medical literature, or both, describing the reasoning which led to the recommendation and references for further consultation by the operator.

The decision support system and method according to the present invention can be implemented as part of a cardiac stimulating device programmer. Thus, the present invention also provides an implantable device programmer capable of delivering programming guidance and decision support. The programmer is preferably capable of using the recommended operating condition to program an implantable cardiac stimulating device via a telemetry head. The programmer can also house a patient/device database unit as described above. Thus, an operator can access a patient's medical history and operating parameters for various implantable cardiac stimulating devices through the programmer's patient/device database, use the decision support feature of the programmer to determine an appropriate setting or operating condition, store the determined settings in the patient/device database, and engage the telemetric capabilities of the programmer to program the implantable device, in a single session with a device programmer according to the present invention.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which.

DETAILED DESCRIPTION OF THE INVENTION

Figure 1:
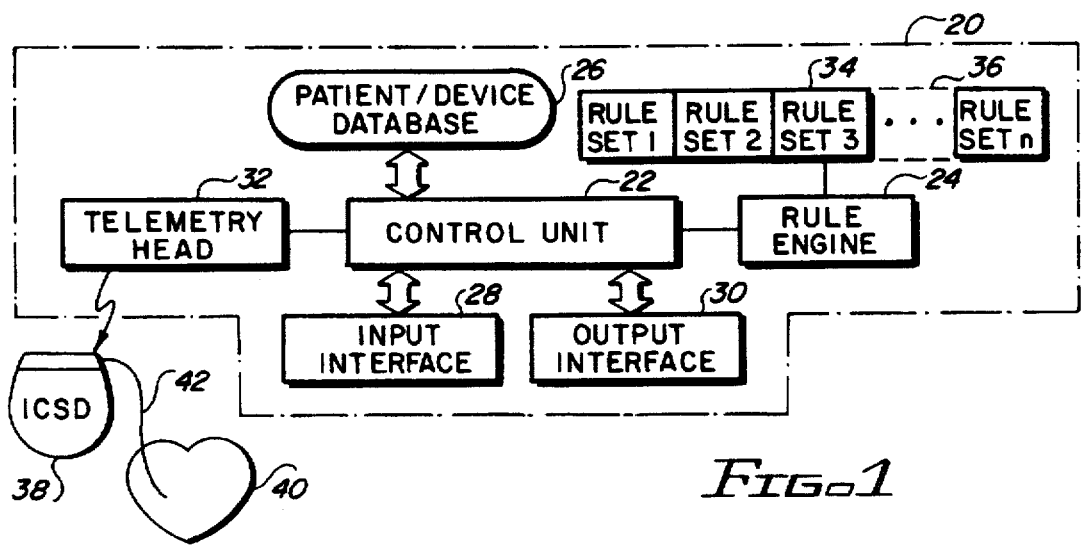
FIG. 1 is a schematic diagram of a preferred embodiment of a decision support system in accordance with the present invention, in which a physician can access a patient/device database, use a rule engine to determine the optimal setting for an adjustable parameter in an implantable cardiac stimulating device, and program the device telemetrically.

The present invention provides a decision support system 20, as shown in FIG. 1, that utilizes a central control unit 22 for the orchestration of tasks among a number of other units and components including a rule engine 24, a patient/device database 26, an input interface 28, an output interface 30, and a telemetry head 32. In addition, the rule engine 24 has access to a number of rule sets 34, stored in a memory unit 36. The control unit is typically microprocessor-based and capable of performing multiple tasks. For example, as shown in FIG. 1, the control unit 22 communicates with an implantable cardiac stimulating device 38 through the telemetry head 32. The telemetry head 32 allows for bidirectional transfer of information. In one direction, the control unit 22 may receive information from the implantable cardiac stimulating device regarding the implantable device itself (e.g., name, model, current parameter settings, etc.) or regarding the operational history of the device and patient response to delivered therapy (e.g., date, energy, and cardiac activity of the patient following the last attempted therapy). In the other direction, the control unit 22 can transmit parameter settings or programming instructions to the implantable cardiac stimulating device and thus affect the operation of the device, if so desired. The implantable device could then stimulate cardiac tissue 40, according to the programmed instructions or parameters, through a conventional lead 42.

In order to determine the optimal parameter settings and programming instructions, the control unit 22 utilizes several auxiliary components. For example, an interface with the patient/device database 26 provides access to further detailed information about patients, and information about implantable devices, that may not be directly available from the implantable device 38. Such data may comprise the medical history of a patient, current drug regimen, and possible susceptibility to certain cardiac arrhythmias. The data may also include information such as guidelines provided by a manufacturer relating to specific device operations, available therapies, and lists of adjustable parameters and specifications for various devices. The data stored in the patient/device database 26 may relate to many different patients and many different implantable cardiac stimulating devices. Thus the decision support system 20 can be used in programming of a variety of different devices for many different patients.

As shown in FIG. 1, the patient/device database 26 may be implemented as part of the decision support system 20 using conventional data storage apparatus, such as a read-only memory cartridge, an optical disk drive, a hard disk drive, a floppy disk drive, a tape drive, or any other suitable data storage device. Alternatively, the database may be separate from the decision support system, as part of an accessory unit such as a mainframe computer in a hospital or any other central database (not shown).

The control unit 22 may also acquire information from the operator of the device such as a physician or a nurse, through the input interface 28. The input interface 28 can be a keyboard, a touch sensitive screen, a screen with a light pen, or any suitable interface that would allow the user to communicate with the control unit 22.

Messages and data can be displayed through the output interface 28, which may be a display monitor, a printer, or any other suitable apparatus for output of information.

The control unit 22 uses a rule engine 24, preferably at least partly microprocessor-based, to provide the operator with suggestions regarding the programming of the implantable device. Although FIG. 1 depicts the control unit 22 and the rule engine 24 as separate units of the decision support system, they can also be implemented with the same microprocessor. Preferably, the rule engine 24 is flexible in that it can operate according to a variety of different rule sets 34, corresponding to different implantable cardiac stimulating devices.

The rule sets 34 are stored in a memory unit 36, which may comprise a read-only memory cartridge, an optical disk drive, a hard disk drive, a floppy disk drive, a tape drive, or any other suitable data storage device. The rule engine 24 is linked to the memory unit 36 so that it can retrieve and load an appropriate rule set according to the instructions of control unit 22. The memory unit 36 may be implemented as part of the patient/device database 26.

Figure 2:
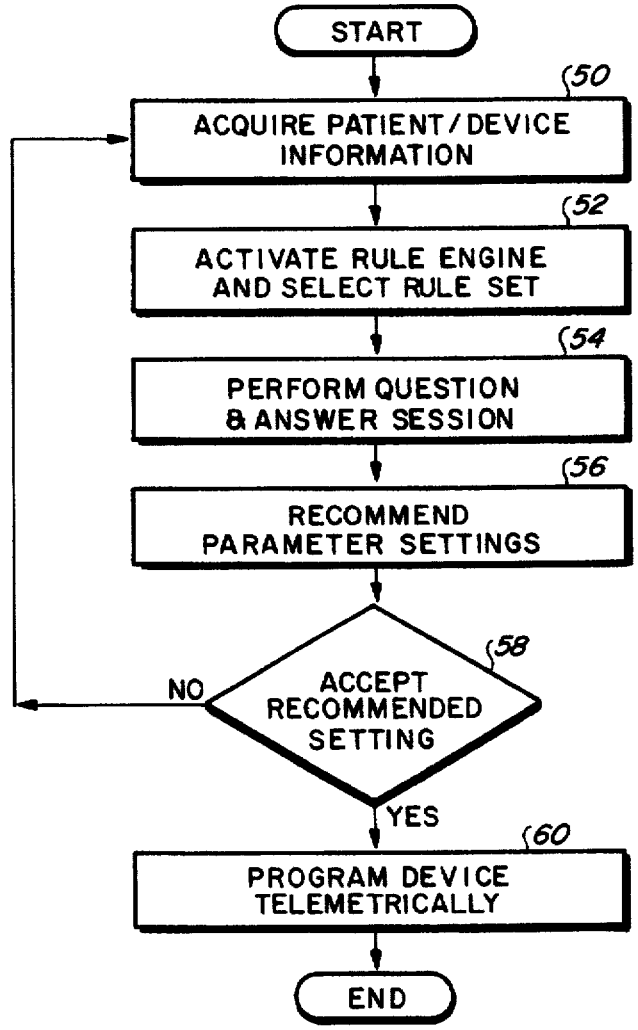
FIG. 2 is a flow chart representing the structure and operation of a preferred embodiment of the decision support system in accordance with the present invention.
Figure 3:
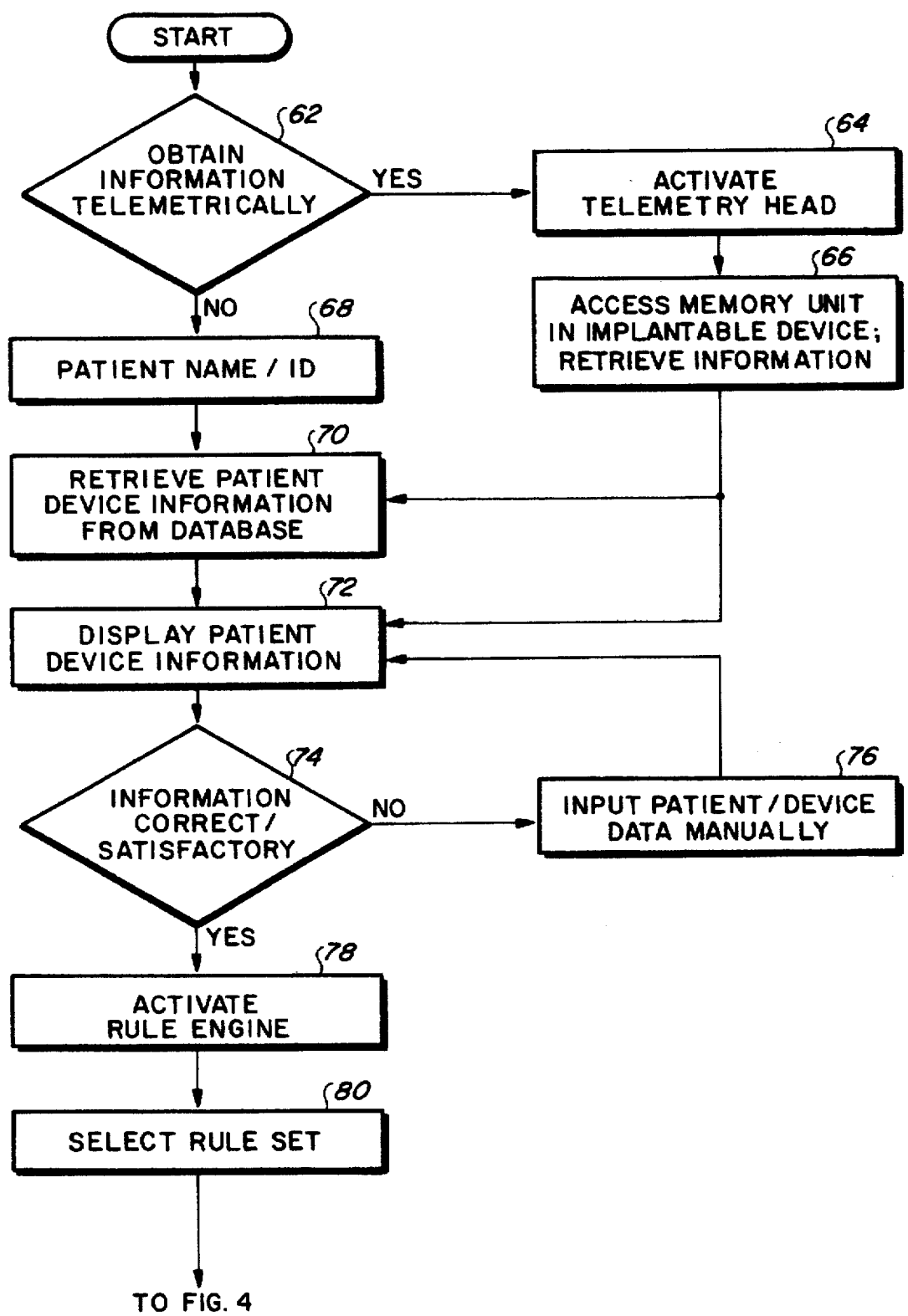
FIGS. 3 and 4 are a flow chart representing the structure of a preferred embodiment of a computer program controlling the operation of the decision support system in accordance with the present invention.
Figure 4:
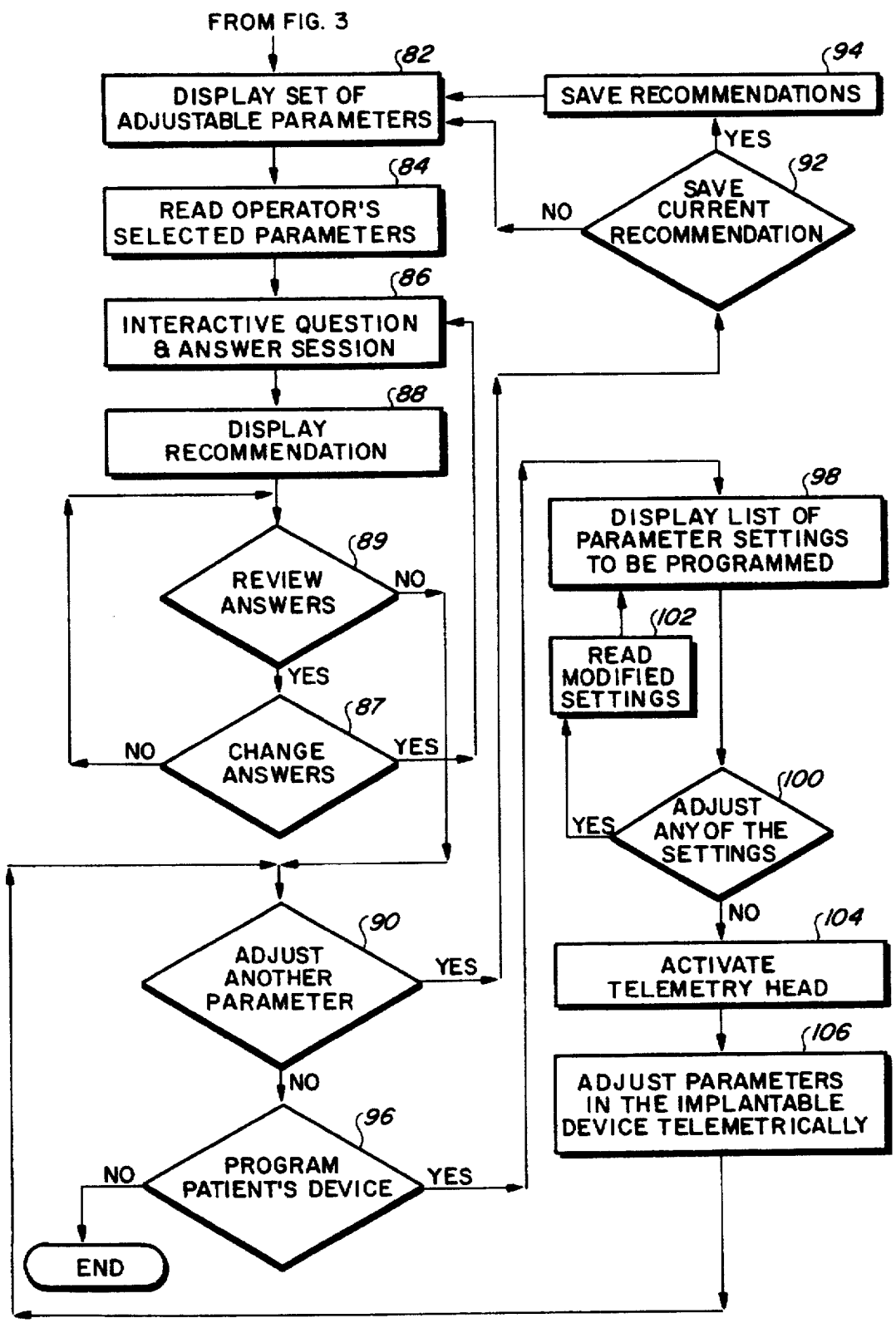

FIGS. 2, 3 and 4 illustrate the decision support system of the present invention under control of a computer program. The program may be implemented in suitable microcode or any higher level computer language. In operation, the computer program causes the system to perform at least five basic tasks as shown schematically in FIG. 2. Initially, the system goes through a data gathering step 50, in which it acquires information regarding the patient (not shown) and the implantable cardiac stimulating device 40 (FIG. 1), that would be required for making a recommendation. Next, at a step 52, the system activates the rule engine 24 (FIG. 1) and, through the rule engine 24, selects an appropriate rule set 34 corresponding to the implantable cardiac stimulating device 40 that is to be programmed (FIG. 1). With the rule engine activated, the system proceeds to a step 54 at which point it guides the operator through an interactive question and answer session. At the step 54, the rule engine determines the questions posed to the operator according to the rule set 34 (FIG. 1) and based on the answers of the operator to previous questions. The session is continued until the rule engine 24 (FIG. 1) can provide a recommendation or set of recommendations from which the physician may choose. At that time, the system advances to a step 56 and displays the recommendation through the output interface 30 (FIG. 1). Any recommendation is preferably accompanied by a list of medical literature references upon which the recommendation is based.

Next, a test 58 is performed to determine whether the operator accepts the recommended setting for programming the device. A "yes" answer leads to a step 60 in which the telemetry head 32 (FIG. 1) is automatically activated and programming instructions are transmitted to the implantable cardiac stimulating device. A "no" answer at test 58, indicating that the operator is not satisfied with the recommendation, returns the system to the step 50 so that the operator can seek another recommendation. A loop encompassing the steps 50–56 and the test 58 can be repeated as many times as required until a satisfactory recommendation is obtained.

FIGS. 3 and 4 provide a more detailed description of the decision support system of this invention under control of a computer program. Here, the operator (not shown) would begin by choosing the mode in which the system is to acquire the desired information. First, at a test 62, the operator is provided with the choice of using the telemetric capabilities of the system to obtain information telemetrically from the implantable cardiac stimulating device 22 (FIG. 1). If so desired (answer "yes" to the test 62), then the system would activate the telemetry head 32 (FIG. 1) at a step 64 and access the memory (not shown) of the implantable cardiac stimulating device 38 (FIG. 1) at a step 66. Depending on the model and specifications of the implantable cardiac stimulating device 38 (FIG. 1), various pieces of information may be stored in its memory. Following step 66, the system would proceed to a step 72 to display the gathered information or, depending on the implementation, proceed to a step 70 to retrieve additional information from the database. This information may include technical information such as a list of parameter settings, or personal data on the patient, such as medical history, and recent cardiac activity as recorded by the device.

Alternatively, the operator may obtain information by accessing the patient/device database 26 (FIG. 1). To do this the system advances to a step 68 in response to a "no" answer to the test 62, and asks for the patient name or an identification number. This can be entered through the input interface 28 (FIG. 1). Having the name or the identification number of the patient, the system can search through the database 26 (FIG. 1) and retrieve whatever pertinent information is available in the database at step 70.

Regardless of the mode of information retrieval (telemetric or database-assisted), all of the gathered information is then displayed for the operator's perusal at step 72. (Alternatively, the operator could be asked to review and accept the data one piece at a time.) A test 74 is performed to determine if the operator finds the retrieved information sufficient and satisfactory. If the answer is "no" (for example, when the medical condition or drug regimen of the patient has changed since the last update of the patient/device database 26 (FIG. 1), or if the operator finds an error in the displayed record), then the system would move to a step 76 and begin to collect the correct and up-to-date information. Input of data by the operator can be facilitated using any known user-friendly data entry protocols. For example, the invention may be practiced using a mouse and menu bars, touch-sensitive screens, or pen-based computers.

Once the correct patient and device information have been gathered, the system activates the rule engine 24 (FIG. 1) at a step 78. The rule engine can then use this information at step 80 to select an appropriate rule set from one of the rule sets 34 (FIG. 1). As noted before, each rule set is marked in the system's memory 36 (FIG. 1) according to the implantable devices to which its rules apply. The appropriate rule set 34 (FIG. 1) may comprise a predefined decision tree, or alternatively, a multitude of interacting rules that are cross-referenced to each other in such a way that they can generate numerous different trees, depending on the order in which different rules are activated. The latter are commonly known as "deduction-oriented" rules or "antecedent-consequent" rule sets.

Regardless of the type of rule-set employed, the system then displays a list of parameters that can be adjusted in the implantable device at a step 82 (FIG. 4). The list is available either from the selected rule set—since each rule set is defined for a particular implantable device—or in an alternative embodiment from the patient/device database 26 (FIG. 1).

The operator is then asked to select, at a step 84, the parameter adjustment for which decision support is requested. (Alternatively, the system may select a default parameter adjustment, thereby not requiring a selection by the operator.) Following the operator's response, the system advances to an interactive question and answer step 86, led by the rule engine 24 (FIG. 1). The operator may select simply "yes" or "no" answers to certain questions or select from multiple-choice answers to others. Each question and possible answers to that question are displayed through the output interface 30 (FIG. 1). Each answer leads the rule engine 24 (FIG. 1) either to a new question, or to a recommendation. When a recommendation has been reached, it is displayed, together with the appropriate literature references, at a step 88. At a test 89, the operator is asked if he would like to review the answers that he had given at step 86 that caused the system to give the recommendation displayed. If the operator answers no, the system proceeds to a test 90. If the operator answers yes at test 89, the system proceeds to a test 87 and displays the answers given previously and asks if the operator would like to modify those answers. If the operator answers yes, the system returns to interactive question and answer step 86. (An additional step could be performed, wherein the operator is asked which answer he would like to modify and the interactive question and answer step 86 is restarted from the corresponding question.) If at test 87, the operator answers no, the system returns to test 89. If at test 89, the operator answered yes, test 90 is performed to determine whether the operator would like another recommendation—either for the adjustment of another parameter, or based on different answers during the question and answer step 86. If the answer is "yes", then the system asks whether the current recommendation should be saved at a test 92. The system is capable of storing several recommendations or programming instructions, so that the operator can collect all the necessary recommendations before programming the implantable cardiac stimulating device 38 (FIG. 1). In this way, the system can avoid piecemeal programming of the implantable cardiac stimulating device 38 (FIG. 1) and it would allow the operator to adjust several parameters all at once. A "yes" answer to the test 92 advances the system to a step 94, at which point the current recommendation is saved, before returning to the step 82 to determine which parameter is to be adjusted next. A "no" answer to the test 92 returns the system to the step 82 directly.

A loop consisting of the steps 82–94 can be repeated until no other recommendations are required. At that point, a "no" response at the test 90 causes the system to proceed to a test 96 which determines whether the operator would like to program the implantable cardiac stimulating device 38 (FIG. 1) telemetrically. If so desired ("yes" answer), the system would automatically display the parameters that it plans to program and the recommended settings at a step 98. At this stage, the operator can use discretion to alter the recommendations of the decision support system before adjusting the implantable cardiac stimulating device 38 (FIG. 1) telemetrically. A test 100 is performed to allow for such alterations. If at test 100 the operator answers "yes", then the preferred settings can be entered at step 102 through the input interface 28 (FIG. 1). When the desired programming parameters have been set, the operator can initiate telemetric programming by entering a "no" answer at the test 100. This causes the system to activate telemetry head 32 (FIG. 1) at a step 104 and adjust the appropriate parameters at a step 106 according to the recommendation(s) made at the step 88.

The system then returns to the test 90 should the operator choose to adjust other parameters in the device, in which case the steps 92–88 are repeated. If not, the answers at tests 90 and 96 would be "no" which brings the program to an end.

Figure 5:
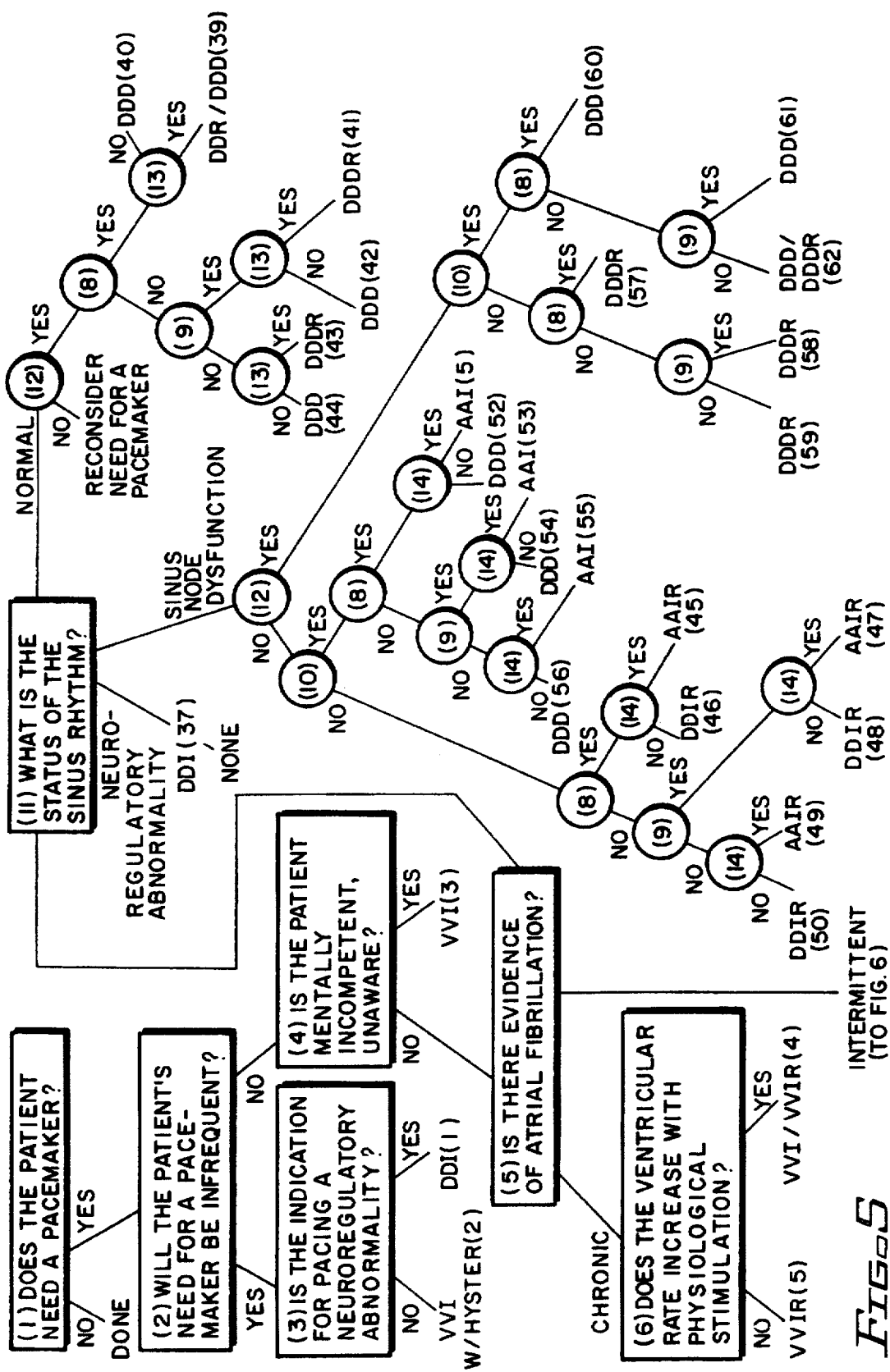
FIGS. 5 and 6 are a schematic representation of a preferred embodiment of a decision tree that can be used as a rule set for reaching a therapy recommendation in accordance with the present invention.
Figure 6:
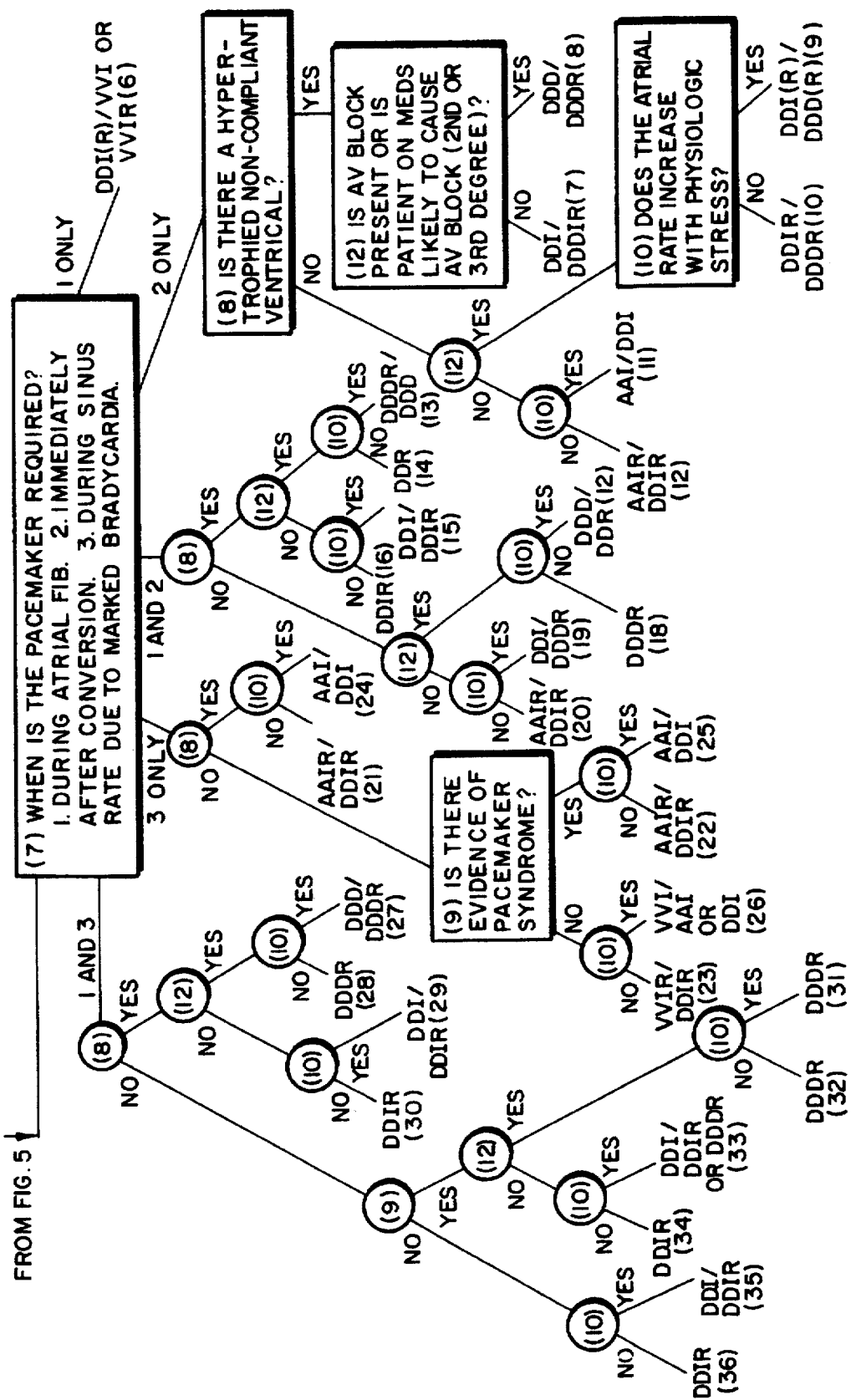

To illustrate further a decision-making process of this invention, FIGS. 5 and 6 show a decision tree that can be used as one of the rule sets 34 (FIG. 1) in the programs represented in FIGS. 2, 3 and 4. This decision tree is an example of a rule set used for making recommendations in adjusting the pacing mode of an implantable pacemaker. However, it would be clear to those skilled in the art that similar decision trees can be easily constructed for adjustment of parameters other than for the pacing mode, and for programming of other implantable cardiac stimulating devices such as an implantable cardioverter or an implantable cardioverter/defibrillator.

As seen in FIGS. 5 and 6, the decision tree provides a "multi-linear" rule set in which questions are organized in a hierarchical fashion. At each branching point or "node," the operator is presented either with a choice of yes/no answers (e.g., at a node 4, FIG. 5) or with multiple choices (e.g., at a node 5, FIG. 5). Each answer determines the next question, and ultimately leads to a recommendation at the outermost tips of the branches of the tree. In the tree of FIGS. 5 and 6, there are 62 such tips corresponding to 62 different recommendations for the adjustable pacing-mode parameter. The descent to each recommendation and the basis for the recommended pacing mode is described in detail in an attached Appendix.

Figure 7:
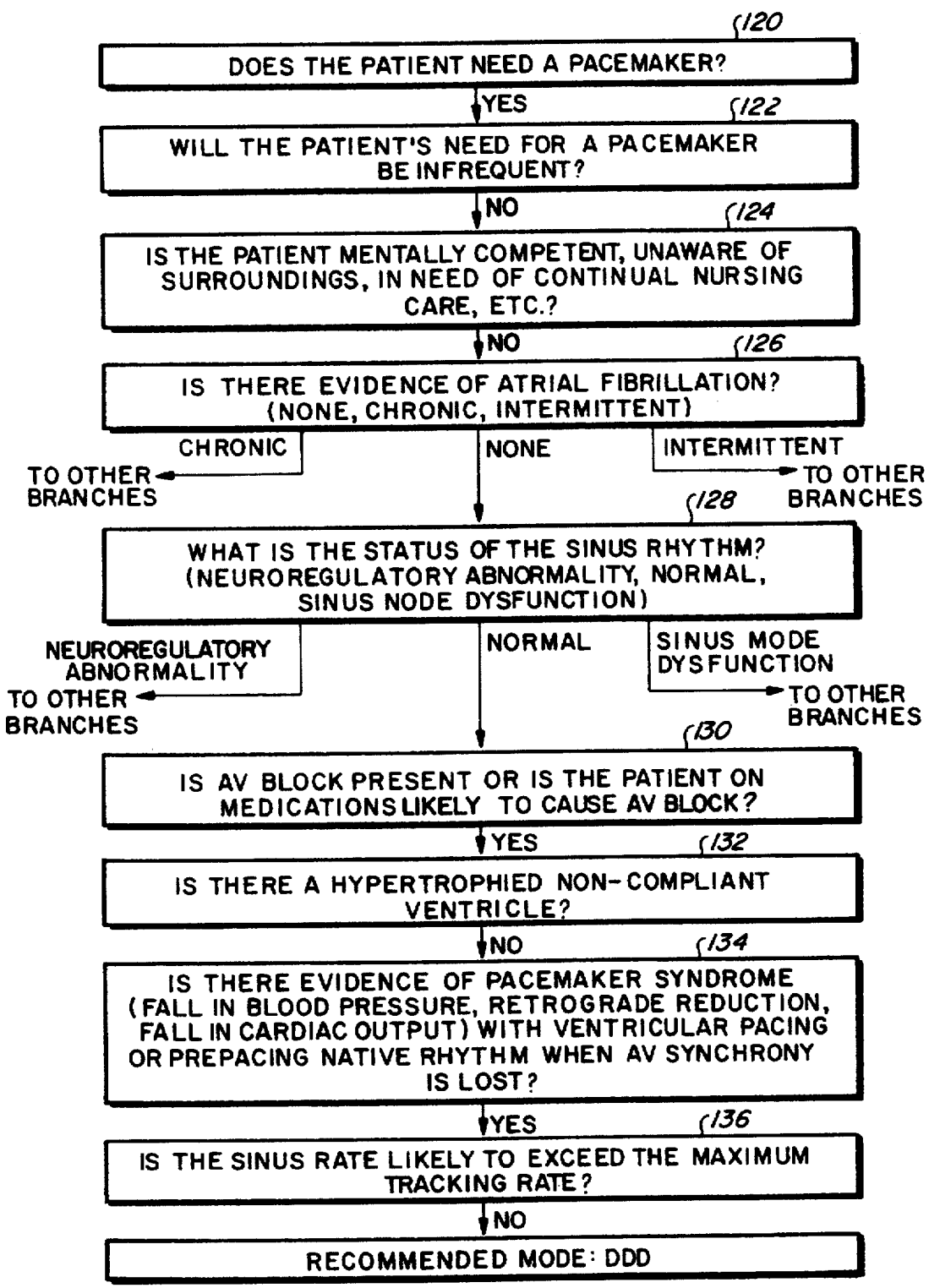
FIG. 7 is a flow chart exemplifying the steps involved in reaching a therapy recommendation in accordance with the decision tree of FIGS. 5 and 6.

To illustrate further the decision making process, FIG. 7 follows the progress of a hypothetical question-and-answer session along one of the branches of the decision tree in FIGS. 5 and 6. This branch corresponds to Mode Selection Conclusion 42 (see appendix). As shown in FIG. 7, the system begins by ascertaining whether the patient needs a pacemaker (node 120), whether the use of the pacemaker would be frequent (node 122), and if the patient is mentally competent (node 124). In this hypothetical case, the patient is a mentally competent subject with frequent need for a pacemaker due to an atrioventricular (AV) block. Therefore, the answers to the questions posed at the nodes 120, 122, and 124 are "yes", "no", and "no", respectively. Although in this example the answers are provided by the operator, they can also be retrieved from the patient/device database 26 (FIG. 1) prior to the question-and-answer session. In that case, the system retrieves answers to as many questions as possible from the database, and then begins to ask for answers to the unanswered questions.

Following the answer to the question of the node 124, the system proceeds to inquire at a node 126 about the possibility of atrial fibrillation at a node 126. The node 126 is an example of a node which can lead to multiple (more than 2) sub-branches. In this case, the answer "none", indicating no evidence of atrial fibrillation, leads to a node 128 which, like the node 126, can lead to multiple sub-branches. When the sinus rhythm is normal, as is the case in the hypothetical example of FIG. 7, the system proceeds to nodes 130–134 to determine if there is possibility of AV block, a hypertrophied non-compliant ventricle, or evidence of pacemaker syndrome. Appropriate answers to these questions lead to a node 136 which determines if a separate sensor (not shown) for rate-responsive pacing should be activated, in case the sinus rate may exceed the maximum tracking rate. Since this is not a concern in this hypothetical case, the answer to the question of the node 136 is "no". At this point the system requires no further information for recommending a pacing-mode, and proceeds to recommend DDD at node 138 (dual-chamber pacing and dual-chamber sensing with rate modulation due to atrial tracking) pacing mode for the hypothetical patient. Significantly, the recommendation for DDD pacing mode is accompanied by the following comments: with documented pacemaker syndrome, whether it being during ventricular pacing or its functional equivalent (a junctive rhythm with loss of AV synchrony, or PVC with retrograde conduction), it is essential to maintain an appropriate atrio-ventricular contraction sequence. For further explanation, the following scientific articles explain the reasoning behind this recommendation: Barold, S., "Cardiac Pacing Hemodynamics: The Pacemaker Syndrome", *Cardio*, (September) 1991; 8:36–51; Heldman, D., et al, "True Incidence of Pacemaking Syndrome", *PACE*, 1990, 13:1742–1750; and Aussbel, U. and Furman, S., "The Pacemaker Syndrome", *Annual of Internal Medicine*, 1985; 103:420–429.

As mentioned previously, the decision tree of FIGS. 5 and 6 provides a multi-linear rule set, which is to say that each of its conclusions (branch tips) is the result of specific answers to a set of questions arranged in a predetermined order. To generate such a tree, a set of questions are ordered, ideally from most general to most specific, and the system would lead the operator through the questions in that order. However, when multiple factors affect the operations of a device interdependently, as in the case for most implantable cardiac stimulating devices, the ranking of different questions becomes an exceedingly difficult and often subjective process. To overcome such problems, the rule sets may arrange a set of questions in an interdependent manner, such that each question appears not in a hierarchical order but depending on the history of the answers given previously.

Thus in some embodiments of the rule sets in accordance with this invention, the order in which questions are posed is neither predetermined nor linear. Such rule sets are well known (see, for example, P. H. Winston *Artificial Intelligence* 2nd Ed., Addison Wesley, pp. 166–204 (1984)) and can be implemented using programming subroutines in artificial intelligence (AI) shells based on any of the well known computer programming languages.

Thus, it is seen that a decision support system is provided that can aid physicians in selection and adjustment of appropriate parameters in implantable cardiac stimulating devices. This decision support system not only aids the physician in optimizing the operations of an implantable cardiac stimulating device, but also provides a bibliographic reference system to facilitate the decision making process. One skilled in the art will appreciate that the present invention can be practiced by other than the described embodiments, which are presented for purposes of illustration and not of limitation, and the present invention is limited only by the claims which follow.

APPENDIX

Mode Selection Conclusion 1

1. Does the patient need a pacemaker?
   Yes.
2. Will the patient's need for a pacemaker be infrequent?
   Yes.
3. Is the indication for pacing a neuroregulatory abnormality such as malignant vasovagal syncope or hypersensitive carotid sinus syndrome?
   Yes.

Recommended Mode: DDI

Comment: These patients usually have a vasodepressor component in addition to bradycardia. They need maintenance of atrial transport in addition to rate support but they do not require atrial pacing [1].

Reference [1]: Fitzpatrick, A. et al., "Dual-Chamber Pacing Aborts Vasovagal Syncope Induced by Headup 60° Tilt," *Pace* 1991; 14; 13–19.

Mode Selection Conclusion 2

1. Does the patient need a pacemaker?
   Yes.
2. Will the patient's need for a pacemaker be infrequent?
   Yes.
3. Is the indication for pacing a neuroregulatory abnormality such as malignant vasovagal syncope or hypersensitive carotid sinus syndrome?
   No.

Recommended Mode: VVI with hysteresis

Comment: VVI with hysteresis will prevent asystole but otherwise prevent the pacemaker from interfering with the patient's intrinsic rhythm. The limitation of this mode is that it does not allow for progression of conduction system disease when pacing may be required frequently at which point restoration of AV synchrony or rate modulation may be of value for the patient.

Mode Selection Conclusion 3
1. Does the patient need a pacemaker?
   Yes.
2. Will the patient's need for a pacemaker be infrequent?
   No.
4. Is the patient mentally incompetent, unaware of surroundings, in need of continual nursing care, etc?
   Yes.

Recommended Mode: VVI

Comment: Despite the very limited functional status of the patient, one should carefully evaluate the effect of ventricular pacing on blood pressure and cardiac output. These patients may have pacemaker syndrome at which time, VVI pacing can worsen this clinical status, and despite their limited functional existence, dual pacing may be necessary if pacing and therapy is recommended.

Mode Selection Conclusion 4
1. Does the patient need a pacemaker?
   Yes.
2. Will the patient's need for a pacemaker be infrequent?
   No.
4. Is the patient mentally incompetent, unaware of surroundings, in need of continual nursing care, etc?
   No.
5. Is there evidence of Atrial fibrillation (None, Chronic, Intermittent)?
   Chronic.
6. Does the Ventricular rate increase with physiologic stress?
   Yes.

Recommended Mode: VVI Alternate: VVIR

Comment: While base rate pacing is all that is required at the time of implantation, progression of AV nodal conduction disease due to intrinsic pathologic processes or medications may render the patient chronotropically incompetent in the future. Rate modulated capability will allow for management of all options.

Mode Selection Conclusion 5
1. Does the patient need a pacemaker?
   Yes.
2. Will the patient's need for a pacemaker be infrequent?
   No.
4. Is the patient mentally incompetent, unaware of surroundings, in need of continual nursing care, etc?
   No.
5. Is there evidence of Atrial fibrillation (None, Chronic, Intermittent)?
   Chronic.
6. Does the Ventricular rate increase with physiologic stress?
   No.

Recommended Mode: VVIR

Comment: In patients whose ventricular rate does not increase with stress, exercise tolerance will be improved with the addition of rate modulation [2].

Given the chronic atrial fibrillation, the only option is single chamber ventricular pacing.

Reference [2]: Humen, D. P. et al., "Activity-Sensing Rate-Responsive Pacing: Improvement in Myocardial Performance with Exercise," *Pace*, 1985; 8: 52–59.

Lau, C. P. et al., "Symptomology and Quality of Life in Patients with Rate-responsive Pacemaker: a Double-Blind Study," *Clinical Cardiology*, 1989; 12: 505–512.

Lau, C. P. et al., "Ventricular Rate-Adaptive Pacing in the Elderly," *European Heart Journal*, 1992; 13: 908–913.

Mode Selection Conclusion 6
1. Does the patient need a pacemaker?
   Yes.
2. Will the patient's need for a pacemaker be infrequent?
   No.
4. Is the patient mentally incompetent, unaware of surroundings, in need of continual nursing care, etc?
   No.
5. Is there evidence of Atrial fibrillation (None, Chronic, Intermittent)?
   Intermittent.
7. When is the pacemaker required?
   1. During Atrial Fib.
   2. Immediately after conversion (i.e. prolonged Sinus Node recovery time)
   3. During Sinus rhythm due to marked bradycardia
   1 only.

Recommended Mode: DDI(R) Alternate: VVI
Second alternative: VVIR

Comment: DDI(R): As the atrial fibrillation is intermittent, one might want to consider the DDI mode. This will not track the fibrillatory wave, but will provide back-up ventricular pacing support when AV Block is present during Atrial Fibrillation. During sinus rhythm, it will provide atrial pacing which may stabilize the atrial rhythm and prevent or minimize the episodes of fibrillation [3].

While base rate pacing is all that is required at the time of implantation, progression of AV nodal conduction disease due to intrinsic pathologic processes or medications may render the patient chronotropically incompetent in the future. Rate modulated capability will allow for management of all options.

For VVI: The patient only needs pacing during atrial fibrillation, hence for AV block at this time, the only mode which will be effective is VVI.

For VVIR: If the level of AV block is persistent during atrial fibrillation, consider a VVIR unit to improve exercise tolerance at these times. However, a VVIR may also increase its rate when the patient is in sinus rhythm, usurping control of the ventricle and induce pacemaker syndrome. The best mode to treat all options is DDIR.

Reference [3]: Bana, G. et al., "DDI Pacing in the Bradycardia-Tachycardia Syndrome," *Pace*, 1990; 13: 264–270.

Markewitz, A. et al., "What is the Most Appropriate Stimulation Mode in Patients with Sinus Node Dysfunction?" *Pace*, 1986; 9: 1115–1120.

Mode Selection Conclusion 7
1. Does the patient need a pacemaker?
   Yes.
2. Will the patient's need for a pacemaker be infrequent?
   No.
4. Is the patient mentally incompetent, unaware of surroundings, in need of continual nursing care, etc?
   No.
5. Is there evidence of Atrial fibrillation (None, Chronic, Intermittent)?
   Intermittent
7. When is the pacemaker required?
   1. During Atrial Fib.
   2. Immediately after conversion (i.e. prolonged Sinus Node recovery time)
   3. During Sinus rhythm due to marked bradycardia 2 only.
8. Is there a hypertrophied, non-compliant ventricle?
Yes.
12. Is AV Block present or is the patient on medications likely to cause AV Block?
No.

Recommended Mode: DDI Alternate: DDIR

Comment: Although AV block is not present initially, pharmacologic therapy needed to control the ventricular response to the atrial fibrillation may unmask AV block, making single chamber AAI pacing unsafe. This same pharmacologic therapy may blunt chronotropic responsiveness warranting rate modulation.

Given the hypertrophied, non-compliant ventricle, one wants to maintain AV synchrony as much as possible when the atrium is NOT fibrillation. Hence VVI and VVIR are not appropriate in this setting.

While base rate pacing is all that is required at the time of implantation, progression of sinus or AV nodal conduction disease due to intrinsic pathologic processes or medications may render the patient chronotropically incompetent in the future. Rate modulated capability will allow for management of all options.

Mode Selection Conclusion 8

1. Does the patient need a pacemaker?
   Yes.
2. Will the patient's need for a pacemaker be infrequent?
   No.
4. Is the patient mentally incompetent, unaware of surroundings, in need of continual nursing care, etc?
   No.
5. Is there evidence of Atrial fibrillation (None, Chronic, Intermittent)?
   Intermittent.
7. When is the pacemaker required?
   1. During Atrial Fib.
   2. Immediately after conversion (i.e. prolonged Sinus Node recovery time)
   3. During Sinus rhythm due to marked bradycardia
   2 only.
8. Is there a hypertrophied, non-compliant ventricle?
   Yes.
12. Is AV Block present or is the patient on medications likely to cause AV Block?
   Yes.

Recommended Mode: DDI Alternate: DDDR

Comment: Pharmacologic therapy needed to control the ventricular response to the atrial fibrillation may exacerbate AV block, making single chamber AAI pacing unsafe. This same pharmacologic therapy may blunt chronotropic responsiveness warranting rate modulation.

As the atrial fibrillation is intermittent, one might want to consider the DDI mode. This will not track the fibrillatory wave, but will provide back-up ventricular pacing support when AV Block is present during atrial fibrillation. During sinus rhythm, it will provide atrial pacing which may stabilize the atrial rhythm and prevent or minimize episodes of fibrillation [3].

As the DDD mode tracks endogenous atrial activity, DDDR is the optimum mode but only when the MTR and MSR can be independently programmed. A low MTR is chosen to minimize the rate increase when the atrial fibrillation. During activity, a high MSR allows an appropriate increase in rate. In the absence of this capability, choose DDIR.

The only time the patient requires pacing is for protection against asystole episodes associated with the prolonged sinus node recovery time following conversion to MSR from atrial fibrillation. Given the concern about AV Block, dual chamber base rate pacing is recommended. However, this does not protect the patient against progression of disease or further compromise from required medications.

Given the hypertrophied, non-complaint ventricle, one wants to maintain AV synchrony as much as possible when the atrium is NOT fibrillation? Hence VVI and VVIR are not appropriate in this setting.

While base rate pacing is all that is required at the time of implantation, progression of sinus or AV nodal conduction disease due to intrinsic pathologic processes or medications may render the patient chronotropically incompetent in the future. Rate modulated capability will allow for management of all options.

Reference [3]: Bana, G. et al., "DDI Pacing in the Bradycardia-Tachycardia Syndrome," Pace, 1990; 13: 264–270.

Markewitz, A. et al., "What is the Most Appropriate Stimulation Mode in Patients with Sinus Mode in Patients with Sinus Node Dysfunction?" Pace, 1986; 9: 1115–1120.

Mode Selection Conclusion 9

1. Does the patient need a pacemaker?
   Yes.
2. Will the patient's need for a pacemaker be infrequent?
   No.
4. Is the patient mentally incompetent, unaware of surroundings, in need of continual nursing care, etc?
   No.
5. Is there evidence of Atrial fibrillation (None, Chronic, Intermittent)?
   Intermittent.
7. When is the pacemaker required?
   1. During Atrial Fib.
   2. Immediately after conversion (i.e. prolonged Sinus Node recovery time)
   3. During Sinus rhythm due to marked bradycardia
   2 only.
8. Is there a hypertrophied, non-compliant ventricle?
   No.
9. Is there evidence of pacemaker syndrome (fall in blood pressure, retrograde conduction, fall in cardiac output) with ventricular pacing or pre-pacing native rhythm when AV synchrony is lost?
   Yes.
12. Is AV Block present or is the patient on medications likely to cause AV Block?
   Yes.
10. Does Atrial rate increase with physiologic stress?
   Yes.

Recommended Mode: DDI(R) Alternate: DDD(R)

Comment: The only time the patient requires pacing is for protection against asystole episodes associated with the prolonged sinus node recovery time following conversion to MSR from atrial fibrillation. Given the concern about AV Block, dual chamber base rate pacing is recommended. However, this does not protect the patient against progression of disease or further compromise from required medications [2].

Pharmacologic therapy needed to control the ventricular response to the atrial fibrillation may exacerbate AV block making single chamber AAI pacing unsafe. This same pharmacologic therapy may blunt chronotropic responsiveness warranting rate modulation.

The persistent sinus bradycardia requires both atrial pacing and rate modulation. As pharmacologic therapy to control the ventricular response to atrial fibrillation, dual chamber pacing in the form of DDIR will provide back-up ventricular support should AV block develop.

With documented pacemaker syndrome—whether it be during ventricular pacing or its functional equivalent (a junctive rhythm with loss of AV synchrony, PVCs: with retrograde conduction) it is essential to maintain an appropriate atrio-ventricular contraction sequence [3].

While base rate pacing is all that is required at the time of implantation, progression of sinus or AV nodal conduction disease due to intrinsic pathologic processes or medications may render the patient chronotropically incompetent in the future. Rate modulated capability will allow for management of all options.

As the DDD mode tracks endogenous atrial activity, DDDR is the optimum mode but only when the MTR and MSR can be independently programmed. A low MTR is chosen to minimize the rate increase when inatrial fibrillation. During activity, a high MSR allows an appropriate increase in rate. In the absence of this capability, choose DDIR.

Reference [3]: Bana, G. et al., "DDI Pacing in the Bradycardia-Tachycardia Syndrome," *Pace*, 1990; 13: 264–270.

Markewitz, A. et al., "What is the Most Appropriate Stimulation Mode in Patients with Sinus Node Dysfunction?" *Pace*, 1986; 9: 1115–1120.

Reference [4]: Barold, S. S., "Cardiac Pacing Hemodynamics: The Pacemaker Syndrome," *Cardio*, 1991; 8: (September) 36–51.

Heldman, D. et al., "True Incidence of Pacemaker Syndrome," *Pace*, 1990; 13: 1742–1750.

Aussbel, U., Furman, S., "The Pacemaker Syndrome, Ann (?) Internal Medicine," 1985; 103: 420–429.

Mode Selection Conclusion 10
1. Does the patient need a pacemaker?
   Yes.
2. Will the patient's need for a pacemaker be infrequent?
   No.
4. Is the patient mentally incompetent, unaware of surroundings, in need of continual nursing care, etc?
   No.
5. Is there evidence of Atrial fibrillation (None, Chronic, Intermittent)?
   Intermittent.
7. When is the pacemaker required?
   1. During Atrial Fib.
   2. Immediately after conversion (i.e. prolonged Sinus Node recovery time)
   3. During Sinus rhythm due to marked bradycardia
   2 only.
8. Is there a hypertrophied, non-compliant ventricle?
   No.
12. Is AV Block present or is the patient on medications likely to cause AV Block?
    Yes.
10. Does Atrial rate increase with physiologic stress?
    No.

Recommended Mode: DDIR Alternate: DDDR

Comment: The persistent sinus bradycardia requires both atrial pacing and rate modulation. As pharmacologic therapy to control the ventricular response to atrial fibrillation, dual chamber pacing in the form of DDIR will provide back-up ventricular support should AV block develop.

As the DDD mode tracks endogenous atrial activity, DDDR is the optimum mode but only when the MTR and MSR can be independently programmed. A low MTR is chosen to minimize the rate increase when inatrial fibrillation. During activity, a high MSR allows an appropriate increase in rate. In the absence of this capability, choose DDIR.

While base rate pacing is all that is required at the time of implantation, progression of AV nodal conduction disease due to intrinsic pathologic processes or medications may render the patient chronotropically incompetent in the future. Rate modulated capability will allow for management of all options.

Mode Selection Conclusion 11
1. Does the patient need a pacemaker?
   Yes.
2. Will the patient's need for a pacemaker be infrequent?
   No.
4. Is the patient mentally incompetent, unaware of surroundings, in need of continual nursing care, etc?
   No.
5. Is there evidence of Atrial fibrillation (None, Chronic, Intermittent)?
   Intermittent.
7. When is the pacemaker required?
   1. During Atrial Fib.
   2. Immediately after conversion (i.e. prolonged Sinus Node recovery time)
   3. During Sinus rhythm due to marked bradycardia
   2 only.
8. Is there a hypertrophied, non-compliant ventricle?
   No.
12. Is AV Block present or is the patient on medications likely to cause AV Block?
    No.
10. Does Atrial rate increase with physiologic stress?
    Yes.

Recommended mode: AAI Alternate: DDI

Comment: The persistent sinus bradycardia requires both atrial pacing and rate modulation. As pharmacologic therapy to control the ventricular response to atrial fibrillation, dual chamber pacing in the form of DDIR will provide back-up ventricular support should AV block develop.

Mode Selection Conclusion 12
1. Does the patient need a pacemaker?
   Yes.
2. Will the patient's need for a pacemaker be infrequent?
   No.
4. Is the patient mentally incompetent, unaware of surroundings, in need of continual nursing care, etc?
   No.
5. Is there evidence of Atrial fibrillation (None, Chronic, Intermittent)?
   Intermittent.
7. When is the pacemaker required?
   1. During Atrial Fib.
   2. Immediately after conversion (i.e. prolonged Sinus Node recovery time)
   3. During Sinus rhythm due to marked bradycardia
   2 only.
8. Is there a hypertrophied, non-compliant ventricle?
   No.
12. Is AV Block present or is the patient on medications likely to cause AV Block?
    No.

10. Does Atrial rate increase with physiologic stress?
No.

Recommended mode: AAIR Alternate: DDIR

Comment: The persistent sinus bradycardia requires both atrial pacing and rate modulation. As pharmacologic therapy to control the ventricular response to atrial fibrillation, dual chamber pacing in the form of DDIR will provide back-up ventricular support should AV block develop.

While base rate pacing is all that is required at the time of implantation, progression of AV nodal conduction disease due to intrinsic pathologic processes or medications may render the patient chronotropically incompetent in the future. Rate modulated capability will allow for management of all options.

Mode Selection Conclusion 13
1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
Intermittent.
7. When is the pacemaker required?
1. During Atrial Fib.
2. Immediately after conversion (i.e. prolonged Sinus Node recovery time)
3. During Sinus rhythm due to marked bradycardia
1 and 2.
8. Is there a hypertrophied, non-compliant ventricle?
Yes.
12. Is AV Block present or is the patient on medications likely to cause AV Block?
Yes.
10. Does Atrial rate increase with physiologic stress?
Yes.

Recommended mode: DDDR Alternate: DDD

Comment: Despite the atrial fibrillation, the presence of AV block mandates DDD pacing. To minimize tracking the high rate during the atrial fibrillation but still allowing for an appropriate rate increase with exercise, choose DDDR in a system with independently programmable MTR and MSR.

As the DDD mode tracks endogenous atrial activity, DDDR is the optimum mode but only when the MTR and MSR can be independently programmed. A low MTR is chosen to minimize the rate increase when the inatrial fibrillation. During activity, a high MSR allows an appropriate increase in rate. In the absence of this capability, choose DDIR.

Given the hypertrophied, non-compliant ventricle, one wants to maintain AV synchrony as much as possible when the atrium is NOT fibrillation. Hence VVI and VVIR are not appropriate in this setting.

Mode Selection Conclusion 14
1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
Intermittent.
7. When is the pacemaker required?
1. During Atrial Fib.
2. Immediately after conversion (i.e. prolonged Sinus Node recovery time)
3. During Sinus rhythm due to marked bradycardia
1 and 2.
8. Is there a hypertrophied, non-compliant ventricle?
Yes.
12. Is AV Block present or is the patient on medications likely to cause AV Block?
Yes.
10. Does Atrial rate increase with physiologic stress?
No.

Recommended mode: DDDR

Comment: Despite the atrial fibrillation, the presence of AV block mandates DDD pacing. To minimize tracking the high rate during the atrial fibrillation but still allowing for an appropriate rate increase with exercise, choose DDDR in a system with independently programmable MTR and MSR.

As the DDD mode tracks endogenous atrial activity, DDDR is the optimum mode but only when the MTR and MSR can be independently programmed. A low MTR is chosen to minimize the rate increase when the atrial fibrillation. During activity, a high MSR allows an appropriate increase in rate. In the absence of this capability, choose DDIR.

Given the hypertrophied, non-compliant ventricle, one wants to maintain AV synchrony as much as possible when the atrium is NOT fibrillation. Hence VVI and VVIR are not appropriate in this setting.

Mode Selection Conclusion 15
1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
Intermittent.
7. When is the pacemaker required?
1. During Atrial Fib.
2. Immediately after conversion (i.e. prolonged Sinus Node recovery time)
3. During Sinus rhythm due to marked bradycardia
1 and 2.
8. Is there a hypertrophied, non-compliant ventricle?
Yes.
12. Is AV Block present or is the patient on medications likely to cause AV Block?
No.
10. Does Atrial rate increase with physiologic stress?
Yes.

Recommended mode: DDI Alternate: DDIR

Comment: The fact that pacing support is required during periods of atrial fibrillation indicating that there is some degree of VA block, even if only at very rapid atrial rates at which time back-up ventricular pacing is required. Thus AAI would not be appropriate in this setting.

As the atrial fibrillation is intermittent, one might want to consider the DDI mode. This will not track the fibrillatory wave, but will provide back-up ventricular pacing support when AV Block is present during atrial fibrillation. During sinus rhythm, it will provide atrial pacing which may stabilize the atrial rhythm and prevent or minimize the episodes of fibrillation [3].

Given the hypertrophied, non-compliant ventricle, one wants to maintain AV synchrony as much as possible when the atrium is NOT fibrillation. Hence VVI and VVIR are not appropriate in this setting.

While base rate pacing is all that is required at the time of implantation, progression of AV nodal conduction disease due to intrinsic pathologic processes or medications may render the patient chronotropically incompetent in the future. Rate modulated capability will allow for management of all options.

Mode Selection Conclusion 16
1. Does the patient need a pacemaker?
   Yes.
2. Will the patient's need for a pacemaker be infrequent?
   No.
4. Is the patient mentally incompetent, unaware of surroundings, in need of continual nursing care, etc?
   No.
5. Is there evidence of Atrial fibrillation (None, Chronic, Intermittent)?
   Intermittent.
7. When is the pacemaker required?
   1. During Atrial Fib.
   2. Immediately after conversion (i.e. prolonged Sinus Node recovery time)
   3. During Sinus rhythm due to marked bradycardia 1 and 2.
8. Is there a hypertrophied, non-compliant ventricle?
   Yes.
12. Is AV Block present or is the patient on medications likely to cause AV Block?
   No.
10. Does Atrial rate increase with physiologic stress?
   No.

Recommended Mode: DDIR

Comment: The fact that pacing support is required during periods of atrial fibrillation indicating that there is some degree of VA block, even if only at very rapid atrial rates at which time back-up ventricular pacing is required. Thus AAI would not be appropriate in this setting.

As the atrial fibrillation is intermittent, one might want to consider the DDI mode. This will not track the fibrillatory wave, but will provide back-up ventricular pacing support when AV Block is present during atrial fibrillation. During sinus rhythm, it will provide atrial pacing which may stabilize the atrial rhythm and prevent or minimize episodes of fibrillation.

Given the hypertrophied, non-compliant ventricle, one wants to maintain AV synchrony as much as possible when the atrium is NOT fibrillation. Hence VVI and VVIR are not appropriate in this setting.

Mode Selection Conclusion 17
1. Does the patient need a pacemaker?
   Yes.
2. Will the patient's need for a pacemaker be infrequent?
   No.
4. Is the patient mentally incompetent, unaware of surroundings, in need of continual nursing care, etc?
   No.
5. Is there evidence of Atrial fibrillation (None, Chronic, Intermittent)?
   Intermittent.
7. When is the pacemaker required?
   1. During Atrial fib.
   2. Immediately after conversion (i.e. prolonged Sinus Node recovery time)
   3. During Sinus rhythm due to marked bradycardia 1 and 2.
8. Is there a hypertrophied, non-compliant ventricle?
   No.
12. Is AV Block present or is the patient on medications likely to cause AV Block?
   Yes.
10. Does Atrial rate increase with physiologic stress?
   Yes.

Recommended Mode: DDD Alternate: DDDR

Comment: Despite the atrial fibrillation, presence of AV block mandates DDD pacing. To minimize tracking the high rate during the atrial fibrillation but still allowing for an appropriate rate increase with exercise, choose DDDR in a system with independently programmable MTR and MSR.

The only time the patient requires pacing is for protection against asystole episodes associated with the prolonged sinus node recovery time following conversion to MSR from atrial fibrillation. Given the concern about AV Block, dual chamber base rate pacing is recommended. However, this does not protect the patient against progression of disease or further compromise from required medications [3].

As the DDD mode tracks endogenous atrial activity, DDDR is the optimum mode but only when the MTR and MSR can be independently programmed. A low MTR is chosen to minimize the rate increase when inatrial fibrillation. During activity, a high MSR allows an appropriate increase in rate. In the absence of this capability, choose DDIR.

While base rate pacing is all that is required at the time of implantation, progression of AV nodal conduction disease due to intrinsic pathologic processes or medications may render the patient chronotropically incompetent in the future. Rate modulated capability will allow for management of all options.

Reference [3]: Bana, G. et al., "DDI Pacing in the Bradycardia-Tachycardia Syndrome," Pace, 1990; 13: 264–270.

Markewitz, A. et al., "What is the Most Appropriate Stimulation Mode in Patients with Sinus Node Dysfunction?" Pace, 1986; 9: 1115–1120.

Mode Selection Conclusion 18
1. Does the patient need a pacemaker?
   Yes.
2. Will the patient's need for a pacemaker be infrequent?
   No.
4. Is the patient mentally incompetent, unaware of surroundings, in need of continual nursing care, etc?
   No.
5. Is there evidence of Atrial fibrillation (None, Chronic, Intermittent)?
   Intermittent.
7. When is the pacemaker required?
   1. During Atrial fib.
   2. Immediately after conversion (i.e. prolonged Sinus Node recovery time)
   3. During Sinus rhythm due to marked bradycardia 1 and 2.
8. Is there a hypertrophied, non-compliant ventricle?
   No.
12. Is AV Block present or is the patient on medications likely to cause AV Block?
   Yes.

10. Does Atrial rate increase with physiologic stress?
No.

Recommended mode: DDDR

Comment: Despite the atrial fibrillation, presence of AV block mandates DDD pacing. To minimize tracking the high rate during the atrial fibrillation but still allowing for an appropriate rate increase with exercise, choose DDDR in a system with independently programmable MTR and MSR.

As the DDD mode tracks endogenous atrial activity, DDDR is the optimum mode but only when the MTR and MSR can be independently programmed. A low MTR is chosen to minimize the rate increase when in atrial fibrillation. During activity, a high MSR allows an appropriate increase in rate. In the absence of this capability, choose DDIR.

Mode Selection Conclusion 19

1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
Intermittent.
7. When is the pacemaker required?
 1. During Atrial fib.
 2. Immediately after conversion (i.e. prolonged Sinus Node recovery time)
 3. During Sinus rhythm due to marked bradycardia
 1 and 2.
8. Is there a hypertrophied, non-compliant ventricle?
No.
12. Is AV Block present or is the patient on medications likely to cause AV Block?
No.
10. Does Atrial rate increase with physiologic stress?
Yes.

Recommended mode: DDI Alternate: DDDR

Comment: The fact that pacing support is required during periods of atrial fibrillation indicating that there is some degree of VA block, even if only at very rapid atrial rates at which time back-up ventricular pacing is required. Thus AAI would not be appropriate in this setting.

While base rate pacing is all that is required at the time of implantation, progression of sinus or AV nodal conduction disease due to intrinsic pathologic processes or medications may render the patient chronotropically incompetent in the future. Rate modulated capability will allow for management of all options.

Mode Selection Conclusion 20

1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
Intermittent.
7. When is the pacemaker required?
 1. During Atrial fib.
 2. Immediately after conversion (i.e. prolonged Sinus Node recovery time)
 3. During Sinus rhythm due to marked bradycardia
 1 and 2.
8. Is there a hypertrophied, non-compliant ventricle?
No.
12. Is AV Block present or is the patient on medications likely to cause AV Block?
No.
10. Does Atrial rate increase with physiologic stress?
No.

Recommended mode: AAIR Alternate: DDIR

Comment: As the DDD mode tracks endogenous atrial activity, DDDR is the optimum mode but only when the MTR and MSR can be independently programmed. A low MTR is chosen to minimize the rate increase when in atrial fibrillation. During activity, a high MSR allows an appropriate increase in rate. In the absence of this capability, choose DDIR.

While base rate pacing is all that is required at the time of implantation, progression of sinus or AV nodal conduction disease due to intrinsic pathologic processes or medications may render the patient chronotropically incompetent in the future. Rate modulated capability will allow for management of all options.

Mode Selection Conclusion 21

1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
Intermittent.
7. When is the pacemaker required?
 1. During Atrial fib.
 2. Immediately after conversion (i.e. elongated Sinus Node recovery time)
 3. During Sinus rhythm due to marked bradycardia
 3 only.
8. Is there a hypertrophied, non-compliant ventricle? Yes.
10. Does Atrial rate increase with physiologic stress?
No.

Recommended mode: AAIR Alternate: DDIR

Comment: Given the hypertrophied, non-compliant ventricle, one wants to maintain AV synchrony as much as possible when the atrium is NOT fibrillation. Hence VVI and VVIR are not appropriate in this setting.

Mode Selection Conclusion 22

1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
Intermittent.
7. When is the pacemaker required?
 1. During Atrial fib.
 2. Immediately after conversion (i.e. elongated Sinus Node recovery time)

3. During Sinus rhythm due to marked bradycardia 3 only.
8. Is there a hypertrophied, non-compliant ventricle?
No.
9. Is there evidence of pacemaker syndrome (fall in blood pressure, retrograde conduction, fall in cardiac output) with ventricular pacing or pre-pacing native rhythm when AV synchrony is lost?
Yes.
10. Does Atrial rate increase with physiologic stress?
No.

Recommended mode: AAIR Alternate: DDIR

Comment: With documented pacemaker syndrome—whether it be during ventricular pacing or its functional equivalent (a junctive rhythm with loss of AV synchrony, PVCS: with retrograde conduction) it is essential to maintain an appropriate atrio-ventricular contraction sequence [4].

Reference [4]: Barold, S. S., "Cardiac Pacing Hemodynamics: The Pacemaker Syndrome," *Cardio*, 1991; (September) 36–51.

Heldman, D. et al., "True Incidence of Pacemaker Syndrome," *Pace*, 1990; 13: 1742–1750.

Aussbel, U., Furman, S., "The Pacemaker Syndrome, Ann (?) Internal Medicine," 1985; 103: 420–429.

Mode Selection Conclusion 23

1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
Intermittent.
6. Does the Ventricular rate increase with physiologic stress?
N/A.
7. When is the pacemaker required?
1. During Atrial fib.
2. Immediately after conversion (i.e. elongated Sinus Node recovery time)
3. During Sinus rhythm due to marked bradycardia 3 only.
8. Is there a hypertrophied, non-compliant ventricle?
No.
9. Is there evidence of pacemaker syndrome (fall in blood pressure, retrograde conduction, fall in cardiac output) with ventricular pacing or pre-pacing native rhythm when AV synchrony is lost?
No.
10. Does Atrial rate increase with physiologic stress?
No.

Recommended mode: VVIR Alternate: DDIR

Mode Selection Conclusion 24

1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
Intermittent.
7. When is the pacemaker required?
1. During Atrial fib.
2. Immediately after conversion (i.e. elongated Sinus Node recovery time)
3. During Sinus rhythm due to marked bradycardia 3 only.
8. Is there a hypertrophied, non-compliant ventricle? Yes.
10. Does Atrial rate increase with physiologic stress?
Yes.

Recommended mode: AAI Alternate: DDI

Comment: Given the hypertrophied, non-compliant ventricle, one wants to maintain AV synchrony as much as possible when the atrium is NOT fibrillation. Hence VVI and VVIR are not appropriate in this setting.

Mode Selection Conclusion 25

1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
Intermittent.
7. When is the pacemaker required?
1. During Atrial fib.
2. Immediately after conversion (i.e. elongated Sinus Node recovery time)
3. During Sinus rhythm due to marked bradycardia 3 only.
8. Is there a hypertrophied, non-compliant ventricle?
No.
9. Is there evidence of pacemaker syndrome (fall in blood pressure, retrograde conduction, fall in cardiac output) with ventricular pacing or pre-pacing native rhythm when AV synchrony is lost?
Yes.
10. Does Atrial rate increase with physiologic stress?
Yes.

Recommended mode: AAI Alternate: DDI

Comment: With documented pacemaker syndrome—whether it be during ventricular pacing or its functional equivalent (a junctive rhythm with loss of AV synchrony, PVCS: with retrograde conduction) it is essential to maintain an appropriate atrio-ventricular contraction sequence [4].

Reference [4]: Barold, S. S., "Cardiac Pacing Hemodynamics: the Pacemaker Syndrome," *Cardio*, 1991; 8: (September) 36–51.

Heldman, D. et al., "True Incidence of Pacemaker Syndrome," *Pace*, 1990; 13: 1742–1750.

Aussbel, U., Furman, S., "The Pacemaker Syndrome, Ann (?) Internal Medicine," 1985; 103: 420–429.

Mode Selection Conclusion 26

1. Does the patient need a pacemaker?
Yes.
2. Will the patient's need for a pacemaker be infrequent
No.
4. Is the patient mentally incompetent, unaware of surroundings, in need of continual nursing care, etc?
No.
5. Is there evidence of Atrial fibrillation (None, Chronic, Intermittent)?

Intermittent.
7. When is the pacemaker required?
    1. During Atrial fib.
    2. Immediately after conversion (i.e. elongated Sinus Node recovery time)
    3. During Sinus rhythm due to marked bradycardia
    3 only.
8. Is there a hypertrophied, non-compliant ventricle?
    No.
9. Is there evidence of pacemaker syndrome (fall in blood pressure, retrograde conduction, fall in cardiac output) with ventricular pacing or pre-pacing native rhythm when AV synchrony is lost?
    No.
10. Does Atrial rate increase with physiologic stress?
    Yes.

Recommended mode: VVI Alternate: AAI, DDI

Mode Selection Conclusion 27
1. Does the patient need a pacemaker?
    Yes.
2. Will the patient's need for a pacemaker be infrequent?
    No.
4. Is the patient mentally incompetent, unaware of surroundings, in need of continual nursing care, etc?
    No.
5. Is there evidence of Atrial fibrillation (None, Chronic, Intermittent)?
    Intermittent.
7. When is the pacemaker required?
    1. During Atrial fib.
    2. Immediately after conversion (i.e. prolonged Sinus Node recovery time)
    3. During Sinus rhythm due to marked bradycardia
    1 and 3.
8. Is there a hypertrophied, non-compliant ventricle?
    Yes.
12. Is AV Block present or is the patient on medications likely to cause AV Block?
    Yes.
10. Does Atrial rate increase with physiologic stress?
    Yes.

Recommended mode: DDD Alternate: DDDR

Comment: As the DDD mode tracks endogenous atrial activity, DDDR is the optimum mode but only when the MTR and MSR can be independently programmed. A low MTR is chosen to minimize the rate increase when in atrial fibrillation. During activity, a high MSR allows an appropriate increase in rate. In the absence of this capability, choose DDIR.

While base rate pacing is all that is required at the time of implantation, progression of sinus or AV nodal conduction disease due to intrinsic pathologic processes or medications may render the patient chronotropically incompetent in the future. Rate modulated capability will allow for management of all options.

Given the hypertrophied, non-compliant ventricle, one wants to maintain AV synchrony as much as possible when the atrium is NOT fibrillation. Hence VVI and VVIR are not appropriate in this setting.

The fact that pacing support is required during periods of atrial fibrillation indicating that there is some degree of VA block, even if only at very rapid atrial rates at which time back-up ventricular pacing is required. Thus AAI would not be appropriate in this setting.

Mode Selection Conclusion 28
1. Does the patient need a pacemaker?
    Yes.
2. Will the patient's need for a pacemaker be infrequent?
    No.
4. Is the patient mentally incompetent, unaware of surroundings, in need of continual nursing care, etc?
    No.
5. Is there evidence of Atrial fibrillation (None, Chronic, Intermittent)?
    Intermittent.
7. When is the pacemaker required?
    1. During Atrial fib.
    2. immediately after conversion (i.e. prolonged Sinus Node recovery time)
    3. During Sinus rhythm due to marked bradycardia
    1 and 3.
8. Is there a hypertrophied, non-compliant ventricle?
    Yes.
12. Is AV Block present or is the patient on medications likely to cause AV Block? Yes.
10. Does Atrial rate increase with physiologic stress?
    No.

Recommended mode: DDDR

Comment: Given the hypertrophied, non-compliant ventricle, one wants to maintain AV synchrony as much as possible when the atrium is NOT fibrillation. Hence VVI and VVIR are not appropriate in this setting.

Mode Selection Conclusion 29
1. Does the patient need a pacemaker?
    Yes.
2. Will the patient's need for a pacemaker be infrequent?
    No.
4. Is the patient mentally incompetent, unaware of surroundings, in need of continual nursing care, etc?
    No.
5. Is there evidence of Atrial fibrillation (None, Chronic, Intermittent)?
    Intermittent.
7. When is the pacemaker required?
    1. During Atrial fib.
    2. Immediately after conversion (i.e. prolonged Sinus Node recovery time)
    3. During Sinus rhythm due to marked bradycardia
    1 and 3.
8. Is there a hypertrophied, non-compliant ventricle?
    Yes.
12. Is AV Block present or is the patient on medications likely to cause AV Block?
    No.
10. Does Atrial rate increase with physiologic stress?
    Yes.

Recommended mode: DDI Alternate: DDIR

Comment: Given the hypertrophied, non-compliant ventricle, one wants to maintain AV synchrony as much as possible when the atrium is NOT fibrillation. Hence VVI and VVIR are not appropriate in this setting.

While base rate pacing is all that is required at the time of implantation, progression of sinus or AV nodal conduction disease due to intrinsic pathologic processes or medications may render the patient chronotropically incompetent in the future. Rate modulated capability will allow for management of all options.

The fact that pacing support is required during periods of atrial fibrillation indicating that there is some degree of VA block, even if only at very rapid atrial rates at which time back-up ventricular pacing is required. Thus AAI would not be appropriate in this setting.

Mode Selection Conclusion 30
1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
Intermittent.
7. When is the pacemaker required?
  1. During Atrial fib.
  2. Immediately after conversion (i.e. prolonged Sinus Node recovery time)
  3. During Sinus rhythm due to marked bradycardia
  1 and 3.
8. Is there a hypertrophied, non-compliant ventricle?
Yes.
12. Is AV Block present or is the patient on medications likely to cause AV Block?
No.
10. Does Atrial rate increase with physiologic stress?
No.
Recommended mode: DDIR Comment: As the DDD mode tracks endogenous atrial activity, DDDR is the optimum mode but only when the MTR and MSR can be independently programmed. A low MTR is chosen to minimize the rate increase when in atrial fibrillation. During activity, a high MSR allows an appropriate increase in rate. In the absence of this capability, choose DDIR.

While base rate pacing is all that is required at the time of implantation, progression of AV nodal conduction disease due to intrinsic pathologic processes or medications may render the patient chronotropically incompetent in the future. A DDDR pacemaker will allow for management of all options.

Given the hypertrophied, non-compliant ventricle, one wants to maintain AV synchrony as much as possible when the atrium is NOT in fibrillation. Hence VVI and VVIR are not appropriate in this setting.

The fact that pacing support is required during periods of atrial fibrillation indicating that there is some degree of VA block, even if only at very rapid atrial rates at which time back-up ventricular pacing is required. Thus AAI would not be appropriate in this setting.

Mode Selection Conclusion 31
1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
Intermittent.
7. When is the pacemaker required?
  1. During Atrial fib.
  2. Immediately after conversion (i.e. prolonged Sinus Node recovery time)
  3. During Sinus rhythm due to marked bradycardia
  1 and 3.
8. Is there a hypertrophied, non-compliant ventricle?
No.
9. Is there evidence of pacemaker syndrome (fall in blood pressure, retrograde conduction, fall in cardiac output) with ventricular pacing or pre-pacing native rhythm when AV synchrony is lost?
Yes.
12. Is AV Block present or is the patient on medications likely to cause AV Block?
Yes.
10. Does Atrial rate increase with physiologic stress?
Yes.
Recommended mode: DDDR Comment: As the DDD mode tracks endogenous atrial activity, DDDR is the optimum mode but only when the MTR and MSR can be independently programmed. A low MTR is chosen to minimize the rate increase when in atrial fibrillation. During activity, a high MSR allows an appropriate increase in rate. In the absence of this capability, choose DDIR.

With documented pacemaker syndrome—whether it being during ventricular pacing or its functional equivalent (a junctive rhythm with loss of AV synchrony, PVC: with retrograde conduction) it is essential to maintain an appropriate atrio-ventricular contraction sequence [4].

Reference [4]: Barold, S. S. "Cardiac Pacing Hemodynamics: The Pacemaker Syndrome," *Cardio*, 1991; 8: (September) 36–51.

Heldman, D. et al., "True Incidence of Pacemaker Syndrome," *Pace*, 1990; 13: 1742–1750.

Aussbel, U., Furman, S., "The Pacemaker Syndrome, Ann (?) Internal Medicine," 1985; 103: 420–429.

Mode Selection Conclusion 32
1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
Intermittent.
7. When is the pacemaker required?
  1. During Atrial fib.
  2. Immediately after conversion (i.e. prolonged Sinus Node recovery time)
  3. During Sinus rhythm due to marked bradycardia
  1 and 3.
8. Is there a hypertrophied, non-compliant ventricle?
No.
9. Is there evidence of pacemaker syndrome (fall in blood pressure, retrograde conduction, fall in cardiac output) with ventricular pacing or pre-pacing native rhythm when AV synchrony is lost?
Yes.
12. Is AV Block present or is the patient on medications likely to cause AV Block?
Yes.
10. Does Atrial rate increase with physiologic stress?
No.
Recommended mode: DDDR Comment: As the DDD mode tracks endogenous atrial activity, DDDR is the optimum mode but only when the MTR and MSR can be independently programmed. A low MTR is chosen to minimize the rate increase when in atrial fibrillation. During activity, a high MSR allows an appropriate increase in rate. In the absence of this capability, choose DDIR.

With documented pacemaker syndrome—whether it being during ventricular pacing or its functional equivalent (a junctive rhythm with loss of AV synchrony, PVC: with retrograde conduction) it is essential to maintain an appropriate atrio-ventricular contraction sequence [4].

Reference [4]: Barold, S. S., "Cardiac Pacing Hemodynamics: the Pacemaker Syndrome," *Cardio*, 1991; 8: (September) 36–51.

Heldman, D. et al., "True Incidence of Pacemaker Syndrome," *Pace*, 1990; 13: 1742–1750.

Aussbel, U., Furman, S., "The Pacemaker Syndrome, Ann (?) Internal Medicine," 1985; 103: 420–429.

Mode Selection Conclusion 33
  1. Does the patient need a pacemaker?
     Yes.
  2. Will the patient's need for a pacemaker be infrequent?
     No.
  4. Is the patient mentally incompetent, unaware of surroundings, in need of continual nursing care, etc?
     No.
  5. Is there evidence of Atrial fibrillation (None, Chronic, Intermittent)?
     Intermittent.
  7. When is the pacemaker required?
     1. During Atrial fib.
     2. immediately after conversion (i.e. prolonged Sinus Node recovery time)
     3. During Sinus rhythm due to marked bradycardia
     1 and 3.
  8. Is there a hypertrophied, non-compliant ventricle?
     No.
  9. Is there evidence of pacemaker syndrome (fall in blood pressure, retrograde conduction, fall in cardiac output) with ventricular pacing or pre-pacing native rhythm when AV synchrony is lost?
     Yes.
  12. Is AV Block present or is the patient on medications likely to cause AV Block?
     No.
  10. Does Atrial rate increase with physiologic stress?
     Yes.

Recommended mode: DDI Alternate: DDIR or DDDR

Comment: As the DDD mode tracks endogenous atrial activity, DDDR is the optimum mode but only when the MTR and MSR can be independently programmed. A low MTR is chosen to minimize the rate increase when in atrial fibrillation. During activity, a high MSR allows an appropriate increase in rate. In the absence of this capability, choose DDIR.

With documented pacemaker syndrome—whether it being during ventricular pacing or its functional equivalent (a junctive rhythm with loss of AV synchrony, PVC: with retrograde conduction) it is essential to maintain an appropriate atrio-ventricular contraction sequence [4].

While base rate pacing is all that is required at the time of implantation, progression of sinus or AV nodal conduction disease due to intrinsic pathologic processes or medications may render the patient chronotropically incompetent in the future. Rate modulated capability will allow for management of all options.

Reference [4]: Barold, S. S., "Cardiac Pacing Hemodynamics: The Pacemaker Syndrome," *Cardio*, 1991; 8: (September) 36–51.

Heldman, D. et al., "True Incidence of Pacemaker Syndrome," *Pace*, 1990; 13: 1742–1750.

Aussbel, U., Furman, S., "The Pacemaker Syndrome, Ann (?) Internal Medicine," 1985; 103: 420–429.

Mode Selection Conclusion 34
  1. Does the patient need a pacemaker?
     Yes.
  2. Will the patient's need for a pacemaker be infrequent?
     No.
  4. Is the patient mentally incompetent, unaware of surroundings, in need of continual nursing care, etc?
     No.
  5. Is there evidence of Atrial fibrillation (None, Chronic, Intermittent)?
     Intermittent.
  7. When is the pacemaker required?
     1. During Atrial fib.
     2. Immediately after conversion (i.e. prolonged Sinus Node recovery time)
     3. During Sinus rhythm due to marked bradycardia
     1 and 3.
  8. Is there a hypertrophied, non-compliant ventricle?
     No.
  9. Is there evidence of pacemaker syndrome (fall in blood pressure, retrograde conduction, fall in cardiac output) with ventricular pacing or pre-pacing native rhythm when AV synchrony is lost?
     Yes.
  12. Is AV Block present or is the patient on medications likely to cause AV Block?
     No.
  10. Does Atrial rate increase with physiologic stress?
     No.

Recommended mode: DDIR

Comment: With documented pacemaker syndrome—whether it being during ventricular pacing or its functional equivalent (a junctive rhythm with loss of AV synchrony, PVC: with retrograde conduction) it is essential to maintain an appropriate atrio-ventricular contraction sequence [4].

The fact that pacing support is required during periods of atrial fibrillation indicating that there is some degree of VA block, even if only at very rapid atrial rates at which time back-up ventricular pacing is required. Thus AAI would not be appropriate in this setting.

Reference [4]: Barold, S. S., "Cardiac Pacing Hemodynamics: The Pacemaker Syndrome," *Cardio*, 1991; 8: (September) 36–51.

Heldman, D. et al., "True Incidence of Pacemaker Syndrome," *Pace*, 1990; 13: 1742–1750.

Aussbel, U., Furman, S., "The Pacemaker Syndrome, Ann (?) Internal Medicine," 1985; 103: 420–429.

Mode Selection Conclusion 35
  1. Does the patient need a pacemaker?
     Yes.
  2. Will the patient's need for a pacemaker be infrequent?
     No.
  4. Is the patient mentally incompetent, unaware of surroundings, in need of continual nursing care, etc?
     No.
  5. Is there evidence of Atrial fibrillation (None, Chronic, Intermittent)?
     Intermittent.
  7. When is the pacemaker required?
     1. During Atrial fib.
     2. Immediately after conversion (i.e. prolonged Sinus Node recovery time)

3. During Sinus rhythm due to marked bradycardia 1 and 3.
8. Is there a hypertrophied, non-compliant ventricle?
No.
9. Is there evidence of pacemaker syndrome (fall in blood pressure, retrograde conduction, fall in cardiac output) with ventricular pacing or pre-pacing native rhythm when AV synchrony is lost?
No.
10. Does Atrial rate increase with physiologic stress?
Yes.

Recommended mode: DDI Alternate: DDIR

Comment: While base rate pacing is all that is required at the time of implantation, progression of sinus or AV nodal conduction disease due to intrinsic pathologic processes or medications may render the patient chronotropically incompetent in the future. Rate modulated capability will allow for management of all options.

The fact that pacing support is required during periods of atrial fibrillation indicating that there is some degree of VA block, even if only at very rapid atrial rates at which time back-up ventricular pacing is required. Thus AAI would not be appropriate in this setting.

Mode Selection Conclusion 36

1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
Intermittent.
7. When is the pacemaker required?
  1. During Atrial fib.
  2. Immediately after conversion (i.e. prolonged Sinus Node recovery time)
  3. During Sinus rhythm due to marked bradycardia 1 and 3.
8. Is there a hypertrophied, non-compliant ventricle?
No.
9. Is there evidence of pacemaker syndrome (fall in blood pressure, retrograde conduction, fall in cardiac output) with ventricular pacing or pre-pacing native rhythm when AV synchrony is lost?
No.
10. Does Atrial rate increase with physiologic stress?
Yes.

Recommended mode: DDI Alternate: DDIR

Comment: While base rate pacing is all that is required at the time of implantation, progression of sinus or AV nodal conduction disease due to intrinsic pathologic processes or medications may render the patient chronotropically incompetent in the future. Rate modulated capability will allow for management of all options.

The fact that pacing support is required during periods of atrial fibrillation indicating that there is some degree of VA block, even if only at very rapid atrial rates at which time back-up ventricular pacing is required. Thus AAI would not be appropriate in this setting.

Mode Selection Conclusion 37

1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
None.
11. What is the status of the sinus rhythm (Neuroregulatory abnormality, Normal, Sinus Node dysfunction)?
Neuroregulatory abnormality.

Recommended mode: DDI

Comment: A neuroregulatory abnormality causes syncope by one of two mechanisms. It inhibits the cardiac rate (both sinus slowing and AV block) and causes vasodilation. Pure cardioinhibitory effects can be treated with VVI pacing. More often, there is a combined mechanism at which time the vasodilation requires AV synchrony to minimize the hypotensive episodes. These patients do not require atrial pacing—hence DDI mode [1].

Reference [1]: Fitzpatrick, A. et al., "Dual-Chamber Pacing Aborts Vasovagal Syncope Induced by Headup 600 Tilt," *Pace* 1991; 14: 13–19.

Mode Selection Conclusion 38

1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
None.
11. What is the status of the sinus rhythm (Neuroregulatory abnormality, Normal, Sinus Node dysfunction)?
Normal.
12. Is AV Block present or is the patient on medications likely to cause AV Block?
No.

Recommended mode: Reconsider need for pacemaker.

Comment: Although the initial decision is that the patient required a pacemaker, based on the answers, there is no evidence for even intermittent sinus node dysfunction or AV block. Unless the pacemaker is being implanted prophylactically in which case answer the questions as if the reason for the pacemaker were manifest; reconsider the decision for permanent cardiac pacing.

Mode Selection Conclusion: 39

1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
None.
11. What is the status of the sinus rhythm (Neuroregulatory abnormality, Normal, Sinus Node dysfunction)?
Normal.

12. Is AV Block present or is the patient on medications likely to cause AV Block?
Yes.

8. Is there a hypertrophied, non-compliant ventricle?
Yes.

13. Is the sinus rate likely to exceed the maximum tracking rate?
Yes.

Recommended mode: DDDR Alternate: DDD

Comment: Although sinus node function may be normal, if the sinus rate exceeds the MTR, the patient may be limited by the loss of appropriate AV synchrony during normal upper rate behavior. Choosing DDDR will allow for sensor-driven rate smoothing [5].

Given the hypertrophied, non-compliant ventricle, one wants to maintain AV synchrony as much as possible when the atrium is NOT fibrillation. Hence VVI and VVIR are not appropriate in this setting.

Reference [5]: Higano, S. T., Hayes, D. L., Elsinger, G., "Sensor-Driven Rate Smoothing in a DDDR Pacemaker," *Pace*, 1989; 12: 922–929.

Mode Selection Conclusion 40

1. Does the patient need a pacemaker?
Yes.

2. Will the patient's need for a pacemaker be infrequent?
No.

4. Is the patient mentally incompetent, unaware of surroundings, in need of continual nursing care, etc?
No.

5. Is there evidence of Atrial fibrillation (None, Chronic, Intermittent)?
None.

11. What is the status of the sinus rhythm (Neuroregulatory abnormality, Normal, Sinus Node dysfunction)?
Normal.

12. Is AV Block present or is the patient on medications likely to cause AV Block?
Yes.

8. Is there a hypertrophied, non-compliant ventricle?
Yes.

13. Is the sinus rate likely to exceed the maximum tracking rate?
No.

Recommended mode: DDD

Comment: Given the hypertrophied, non-compliant ventricle, one wants to maintain AV synchrony as much as possible when the atrium is NOT fibrillation. Hence VVI and VVIR are not appropriate in this setting.

Mode Selection Conclusion 41

1. Does the patient need a pacemaker?
Yes.

2. Will the patient's need for a pacemaker be infrequent?
No.

4. Is the patient mentally incompetent, unaware of surroundings, in need of continual nursing care, etc?
No.

5. Is there evidence of Atrial fibrillation (None, Chronic, Intermittent)?
None.

11. What is the status of the sinus rhythm (Neuroregulatory abnormality, Normal, Sinus Node dysfunction)?
Normal.

12. Is AV Block present or is the patient on medications likely to cause AV Block?
Yes.

8. Is there a hypertrophied, non-compliant ventricle?
No.

9. Is there evidence of pacemaker syndrome (fall in blood pressure, retrograde conduction, fall in cardiac output) with ventricular pacing or pre-pacing native rhythm when AV synchrony is lost?
Yes.

13. Is the sinus rate likely to exceed the maximum tracking rate?
Yes.

Recommended mode: DDDR Patient Disc:

Comment: With documented pacemaker syndrome—whether it being during ventricular pacing or its functional equivalent (a junctive rhythm with loss of AV synchrony, PVC: with retrograde conduction) it is essential to maintain an appropriate atrio-ventricular contraction sequence [4].

Reference [4]: Barold, S. S., "Cardiac Pacing Hemodynamics: The Pacemaker Syndrome," *Cardio*, 1991; 8: (September) 36–51.

Heldman, D. et al., "True Incidence of Pacemaker Syndrome," *Pace*, 1990; 13: 1742–1750.

Aussbel, U., Furman, S., "The Pacemaker Syndrome, Ann (?) Internal Medicine," 1985; 103: 420–429.

Mode Selection Conclusion 42

1. Does the patient need a pacemaker?
Yes.

2. Will the patient's need for a pacemaker be infrequent?
No.

4. Is the patient mentally incompetent, unaware of surroundings, in need of continual nursing care, etc?
No.

5. Is there evidence of Atrial fibrillation (None, Chronic, Intermittent)?
None.

11. What is the status of the sinus rhythm (Neuroregulatory abnormality, Normal, Sinus Node dysfunction)?
Normal.

12. Is AV Block present or is the patient on medications likely to cause AV Block?
Yes.

8. Is there a hypertrophied, non-compliant ventricle?
No.

9. Is there evidence of pacemaker syndrome (fall in blood pressure, retrograde conduction, fall in cardiac output) with ventricular pacing or pre-pacing native rhythm when AV synchrony is lost?
Yes.

13. Is the sinus rate likely to exceed the maximum tracking rate?
No.

Recommended mode: DDD

Patient Disc:

Comment: With documented pacemaker syndrome—whether it being during ventricular pacing or its functional equivalent (a junctive rhythm with loss of AV synchrony, PVC: with retrograde conduction) it is essential to maintain an appropriate atrio-ventricular contraction sequence [4].

Reference [4]: Barold, S. S., "Cardiac Pacing Hemodynamics: The Pacemaker Syndrome," *Cardio*, 1991; 8: (September) 36–51.

Heldman, D. et al., "True Incidence of Pacemaker Syndrome," *Pace*, 1990; 13: 1742–1750.

Aussbel, U., Furman, S., "The Pacemaker Syndrome, Ann (?) Internal Medicine," 1985; 103: 420–429.

Mode Selection Conclusion 43
 1. Does the patient need a pacemaker?
 Yes.
 2. Will the patient's need for a pacemaker be infrequent?
 No.
 4. Is the patient mentally incompetent, unaware of surroundings, in need of continual nursing care, etc?
 No.
 5. Is there evidence of Atrial fibrillation (None, Chronic, Intermittent)?
 None.
 11. What is the status of the sinus rhythm (Neuroregulatory abnormality, Normal, Sinus Node dysfunction)?
 Normal.
 12. Is AV Block present or is the patient on medications likely to cause AV Block?
 Yes.
 8. Is there a hypertrophied, non-compliant ventricle?
 No.
 9. Is there evidence of pacemaker syndrome (fall in blood pressure, retrograde conduction, fall in cardiac output) with ventricular pacing or pre-pacing native rhythm when AV synchrony is lost?
 No.
 13. Is the sinus rate likely to exceed the maximum tracking rate?
 Yes.
Recommended mode: DDDR Mode Selection Conclusion 44
 1. Does the patient need a pacemaker?
 Yes.
 2. Will the patient's need for a pacemaker be infrequent?
 No.
 4. Is the patient mentally incompetent, unaware of surroundings, in need of continual nursing care, etc?
 No.
 5. Is there evidence of Atrial fibrillation (None, Chronic, Intermittent)?
 None.
 11. What is the status of the sinus rhythm (Neuroregulatory abnormality, Normal, Sinus Node dysfunction)?
 Normal.
 12. Is AV Block present or is the patient on medications likely to cause AV Block?
 Yes.
 8. Is there a hypertrophied, non-compliant ventricle?
 No.
 9. Is there evidence of pacemaker syndrome (fall in blood pressure, retrograde conduction, fall in cardiac output) with ventricular pacing or pre-pacing native rhythm when AV synchrony is lost?
 No.
 13. Is the sinus rate likely to exceed the maximum tracking rate?
 No.
Recommended mode: DDD Mode Selection Conclusion 45
 1. Does the patient need a pacemaker?
 Yes.
 2. Will the patient's need for a pacemaker be infrequent?
 No.
 4. Is the patient mentally incompetent, unaware of surroundings, in need of continual nursing care, etc?
 No.
 5. Is there evidence of Atrial fibrillation (None, Chronic, Intermittent)?
 None.
 11. What is the status of the sinus rhythm (Neuroregulatory abnormality, Normal, Sinus Node dysfunction)?
 Sinus Node dysfunction.
 12. Is AV Block present or is the patient on medications likely to cause AV Block?
 No.
 10. Does Atrial rate increase with physiologic stress?
 No.
 8. Is there a hypertrophied, non-compliant ventricle?
 Yes.
 14. Is AV node function normal even at higher rates?
 Yes.
Recommended mode: AAIR
Comment: Given the hypertrophied, non-compliant ventricle, one wants to maintain AV synchrony as much as possible when the atrium is NOT fibrillation. Hence VVI and VVIR are not appropriate in this setting.

Mode Selection Conclusion 46
 1. Does the patient need a pacemaker?
 Yes.
 2. Will the patient's need for a pacemaker be infrequent?
 No.
 4. Is the patient mentally incompetent, unaware of surroundings, in need of continual nursing care, etc?
 No.
 5. Is there evidence of Atrial fibrillation (None, Chronic, Intermittent)?
 None.
 11. What is the status of the sinus rhythm (Neuroregulatory abnormality, Normal, Sinus Node dysfunction)?
 Sinus Node dysfunction.
 12. Is AV Block present or is the patient on medications likely to cause AV Block?
 No.
 10. Does Atrial rate increase with physiologic stress?
 No.
 8. Is there a hypertrophied, non-compliant ventricle?
 Yes.
 14. Is AV node function normal even at higher rates?
 No.
Recommended mode: DDIR
Comment: Given the hypertrophied, non-compliant ventricle, one wants to maintain AV synchrony as much as possible when the atrium is NOT fibrillation. Hence VVI and VVIR are not appropriate in this setting.

Mode Selection Conclusion 47
 1. Does the patient need a pacemaker?
 Yes.
 2. Will the patient's need for a pacemaker be infrequent?
 No.
 4. Is the patient mentally incompetent, unaware of surroundings, in need of continual nursing care, etc?
 No.
 5. Is there evidence of Atrial fibrillation (None, Chronic, Intermittent)?
 None.

11. What is the status of the sinus rhythm (Neuroregulatory abnormality, Normal, Sinus Node dysfunction)?
Sinus Node dysfunction.

12. Is AV Block present or is the patient on medications likely to cause AV Block?
No.

10. Does Atrial rate increase with physiologic stress?
No.

8. Is there a hypertrophied, non-compliant ventricle?
No.

9. Is there evidence of pacemaker syndrome (fall in blood pressure, retrograde conduction, fall in cardiac output) with ventricular pacing or pre-pacing native rhythm when AV synchrony is lost?
Yes.

14. Is AV node function normal even at higher rates?
Yes.

Recommended mode: AAIR Patient Disc:

Comment: With documented pacemaker syndrome whether it being during ventricular pacing or its functional equivalent (a junctive rhythm with loss of AV synchrony, PVC: with retrograde conduction) it is essential to maintain an appropriate atrio-ventricular contraction sequence [4].

Reference [4]: Barold, S. S., "Cardiac Pacing Hemodynamics: The Pacemaker Syndrome," *Cardio*, 1991; 8: (September) 36–51.

Heldman, D. et al., "True Incidence of Pacemaker Syndrome," *Pace*, 1990; 13: 1742–1750.

Aussbel, U., Furman, S., "The Pacemaker Syndrome, Ann (?) Internal Medicine," 1985; 103: 420–429.

Mode Selection Conclusion 48

1. Does the patient need a pacemaker?
Yes.

2. Will the patient's need for a pacemaker be infrequent?
No.

4. Is the patient mentally incompetent, unaware of surroundings, in need of continual nursing care, etc?
No.

5. Is there evidence of Atrial fibrillation (None, Chronic, Intermittent)?
None.

11. What is the status of the sinus rhythm (Neuroregulatory abnormality, Normal, Sinus Node dysfunction)?
Sinus Node dysfunction 12. Is AV Block present or is the patient on medications likely to cause AV Block?
No.

10. Does Atrial rate increase with physiologic stress?
No.

8. Is there a hypertrophied, non-compliant ventricle?
No.

9. Is there evidence of pacemaker syndrome (fall in blood pressure, retrograde conduction, fall in cardiac output) with ventricular pacing or pre-pacing native rhythm when AV synchrony is lost?
Yes.

14. Is AV node function normal even at higher rates?
No.

Recommended mode: DDIR Patient Disc:

Comment: With documented pacemaker syndrome whether it being during ventricular pacing or its functional equivalent (a junctive rhythm with loss of AV synchrony, PVC: with retrograde conduction) it is essential to maintain an appropriate atrio-ventricular contraction sequence [4].

Reference [4]: Barold, S. S., "Cardiac Pacing Hemodynamics: The Pacemaker Syndrome," *Cardio*, 1991; 08: (September) 36–51.

Heldman, D. et al., "True Incidence of Pacemaker Syndrome," *Pace*, 1990; 13: 1742–1750.

Aussbel, U., Furman, S., "The Pacemaker Syndrome, Ann (?) Internal Medicine," 1985; 103: 420–429.

Mode Selection Conclusion 49

1. Does the patient need a pacemaker?
Yes.

2. Will the patient's need for a pacemaker be infrequent?
No.

4. Is the patient mentally incompetent, unaware of surroundings, in need of continual nursing care, etc?
No.

5. Is there evidence of Atrial fibrillation (None, Chronic, Intermittent)?
None.

11. What is the status of the sinus rhythm (Neuroregulatory abnormality, Normal, Sinus Node dysfunction)?
Sinus Node dysfunction.

12. Is AV Block present or is the patient on medications likely to cause AV Block?
No.

10. Does Atrial rate increase with physiologic stress?
No.

8. Is there a hypertrophied, non-compliant ventricle?
No.

9. Is there evidence of pacemaker syndrome (fall in blood pressure, retrograde conduction, fall in cardiac output) with ventricular pacing or pre-pacing native rhythm when AV synchrony is lost?
No.

14. Is AV node function normal even at higher rates?
Yes.

Recommended mode: AAIR
Mode Selection Conclusion 50

1. Does the patient need a pacemaker?
Yes.

2. Will the patient's need for a pacemaker be infrequent?
No.

4. Is the patient mentally incompetent, unaware of surroundings, in need of continual nursing care, etc?
No.

5. Is there evidence of Atrial fibrillation (None, Chronic, Intermittent)?
None.

11. What is the status of the sinus rhythm (Neuroregulatory abnormality, Normal, Sinus Node dysfunction)?
Sinus Node dysfunction.

12. Is AV Block present or is the patient on medications likely to cause AV Block?
No.

10. Does Atrial rate increase with physiologic stress?
No.

8. Is there a hypertrophied, non-compliant ventricle?
No.

9. Is there evidence of pacemaker syndrome (fall in blood pressure, retrograde conduction, fall in cardiac output) with ventricular pacing or pre-pacing native rhythm when AV synchrony is lost?
No.

14. Is AV node function normal even at higher rates?
No.

Recommended mode: DDIR

Mode Selection Conclusion 51

1. Does the patient need a pacemaker?
Yes.

2. Will the patient's need for a pacemaker be infrequent?
No.

4. Is the patient mentally incompetent, unaware of surroundings, in need of continual nursing care, etc?
No.

5. Is there evidence of Atrial fibrillation (None, Chronic, Intermittent)?
None.

11. What is the status of the sinus rhythm (Neuroregulatory abnormality, Normal, Sinus Node dysfunction)?
Sinus Node dysfunction.

12. Is AV Block present or is the patient on medications likely to cause AV Block?
No.

10. Does Atrial rate increase with physiologic stress?
Yes.

8. Is there a hypertrophied, non-compliant ventricle?
Yes.

14. Is AV node function normal even at higher rates?
Yes.

Recommended Mode: AAI

Comment: Given the hypertrophied, non-compliant ventricle, one wants to maintain AV synchrony as much as possible when the atrium is NOT fibrillation. Hence VVI and VVIR are not appropriate in this setting.

Mode Selection Conclusion 52

1. Does the patient need a pacemaker?
Yes.

2. Will the patient's need for a pacemaker be infrequent?
No.

4. Is the patient mentally incompetent, unaware of surroundings, in need of continual nursing care, etc?
No.

5. Is there evidence of Atrial fibrillation (None, Chronic, Intermittent)?
None.

11. What is the status of the sinus rhythm (Neuroregulatory abnormality, Normal, Sinus Node dysfunction)?
Sinus Node dysfunction.

12. Is AV Block present or is the patient on medications likely to cause AV Block?
No.

10. Does Atrial rate increase with physiologic stress?
Yes.

8. Is there a hypertrophied, non-compliant ventricle?
Yes.

14. Is AV node function normal even at higher rates?
No.

Recommended Mode: DDD

Comment: Given the hypertrophied, non-compliant ventricle, one wants to maintain AV synchrony as much as possible when the atrium is NOT fibrillation. Hence VVI and VVIR are not appropriate in this setting.

Mode Selection Conclusion 53

1. Does the patient need a pacemaker?
Yes.

2. Will the patient's need for a pacemaker be infrequent?
No.

4. Is the patient mentally incompetent, unaware of surroundings, in need of continual nursing care, etc?
No.

5. Is there evidence of Atrial fibrillation (None, Chronic, Intermittent)?
None.

11. What is the status of the sinus rhythm (Neuroregulatory abnormality, Normal, Sinus Node dysfunction)?
Sinus Node dysfunction.

12. Is AV Block present or is the patient on medications likely to cause AV Block?
No.

10. Does Atrial rate increase with physiologic stress?
Yes.

8. Is there a hypertrophied, non-compliant ventricle?
No.

9. Is there evidence of pacemaker syndrome (fall in blood pressure, retrograde conduction, fall in cardiac output) with ventricular pacing or pre-pacing native rhythm when AV synchrony is lost?
Yes.

14. Is AV node function normal even at higher rates?
Yes.

Recommended mode: AAI Patient Disc:

Comment: With documented pacemaker syndrome—whether it being during ventricular pacing or its functional equivalent (a junctive rhythm with loss of AV synchrony, PVC: with retrograde conduction) it is essential to maintain an appropriate atrio-ventricular contraction sequence [4].

Reference [4]: Barold, S. S., "Cardiac Pacing Hemodynamics: The Pacemaker Syndrome," *Cardio*, 1991; 8: (September) 36–51.

Heldman, D. et al., "True Incidence of Pacemaker Syndrome," *Pace*, 1990; 13: 1742–1750.

Aussbel, U., Furman, S., "The Pacemaker Syndrome, Ann (?) Internal Medicine," 1985; 103: 420–429.

Mode Selection Conclusion 54

1. Does the patient need a pacemaker?
Yes.

2. Will the patient's need for a pacemaker be infrequent?
No.

4. Is the patient mentally incompetent, unaware of surroundings, in need of continual nursing care, etc?
No.

5. Is there evidence of Atrial fibrillation (None, Chronic, Intermittent)?
None.

11. What is the status of the sinus rhythm (Neuroregulatory abnormality, Normal, Sinus Node dysfunction)?
Sinus Node dysfunction.

12. Is AV Block present or is the patient on medications likely to cause AV Block?
No.

10. Does Atrial rate increase with physiologic stress?
Yes.

8. Is there a hypertrophied, non-compliant ventricle?
No.

9. Is there evidence of pacemaker syndrome (fall in blood pressure, retrograde conduction, fall in cardiac output)

with ventricular pacing or pre-pacing native rhythm when AV synchrony is lost?
Yes.

14. Is AV node function normal even at higher rates?
No.

Recommended Mode: DDD

Comment: With documented pacemaker syndrome—whether it being during ventricular pacing or its functional equivalent (a junctive rhythm with loss of AV synchrony, PVC: with retrograde conduction) it is essential to maintain an appropriate atrio-ventricular contraction sequence [4].

Reference [4]: Barold, S. S., "Cardiac Pacing Hemodynamics: The Pacemaker Syndrome," *Cardio*, 1991; 8: (September) 36–51.

Heldman, D. et al., "True Incidence of Pacemaker Syndrome," *Pace*, 1990; 13: 1742–1750.

Aussbel, U., Furman, S., "The Pacemaker Syndrome, Ann (?) Internal Medicine," 1985; 103: 420–429.

Mode Selection Conclusion 55

1. Does the patient need a pacemaker?
Yes.

2. Will the patient's need for a pacemaker be infrequent?
No.

4. Is the patient mentally incompetent, unaware of surroundings, in need of continual nursing care, etc?
No.

5. Is there evidence of Atrial fibrillation (None, Chronic, Intermittent)?
None.

11. What is the status of the sinus rhythm (Neuroregulatory abnormality, Normal, Sinus Node dysfunction)?
Sinus Node dysfunction 12. Is AV Block present or is the patient on medications likely to cause AV Block?
No.

10. Does Atrial rate increase with physiologic stress?
Yes.

8. Is there a hypertrophied, non-compliant ventricle?
No.

9. Is there evidence of pacemaker syndrome (fall in blood pressure, retrograde conduction, fall in cardiac output) with ventricular pacing or pre-pacing native rhythm when AV synchrony is lost?
No.

14. Is AV node function normal even at higher rates?
Yes.

Recommended Mode: AAI

Mode Selection Conclusion 56

1. Does the patient need a pacemaker?
Yes.

2. Will the patient's need for a pacemaker be infrequent?
No.

4. Is the patient mentally incompetent, unaware of surroundings, in need of continual nursing care, etc?
No.

5. Is there evidence of Atrial fibrillation (None, Chronic, Intermittent)?
None.

11. What is the status of the sinus rhythm (Neuroregulatory abnormality, Normal, Sinus Node dysfunction)?
Sinus Node dysfunction.

12. Is AV Block present or is the patient on medications likely to cause AV Block?
No.

10. Does Atrial rate increase with physiologic stress?
Yes.

8. Is there a hypertrophied, non-compliant ventricle?
No.

9. Is there evidence of pacemaker syndrome (fall in blood pressure, retrograde conduction, fall in cardiac output) with ventricular pacing or pre-pacing native rhythm when AV synchrony is lost?
No.

14. Is AV node function normal even at higher rates?
No.

Recommended Mode: DDD

Mode Selection Conclusion 57

1. Does the patient need a pacemaker?
Yes.

2. Will the patient's need for a pacemaker be infrequent?
No.

4. Is the patient mentally incompetent, unaware of surroundings, in need of continual nursing care, etc?
No.

5. Is there evidence of Atrial fibrillation (None, Chronic, Intermittent)?
None.

11. What is the status of the sinus rhythm (Neuroregulatory abnormality, Normal, Sinus Node dysfunction)?
Sinus Node dysfunction 12. Is AV Block present or is the patient on medications likely to cause AV Block?
Yes.

10. Does Atrial rate increase with physiologic stress?
No.

8. Is there a hypertrophied, non-compliant ventricle?
Yes.

Recommended Mode: DDDR

Comment: Given the hypertrophied, non-compliant ventricle, one wants to maintain AV synchrony as much as possible when the atrium is NOT fibrillation. Hence VVI and VVIR are not appropriate in this setting.

Mode Selection Conclusion 58

1. Does the patient need a pacemaker?
Yes.

2. Will the patient's need for a pacemaker be infrequent?
No.

4. Is the patient mentally incompetent, unaware of surroundings, in need of continual nursing care, etc?
No.

5. Is there evidence of Atrial fibrillation (None, Chronic, Intermittent)?
None.

11. What is the status of the sinus rhythm (Neuroregulatory abnormality, Normal, Sinus Node dysfunction)?
Sinus Node dysfunction 12. Is AV Block present or is the patient on medications likely to cause AV Block?
Yes.

10. Does Atrial rate increase with physiologic stress?
No.

8. Is there a hypertrophied, non-compliant ventricle?
No.

9. Is there evidence of pacemaker syndrome (fall in blood pressure, retrograde conduction, fall in cardiac output)

with ventricular pacing or pre-pacing native rhythm when AV synchrony is lost?
Yes.
Recommended mode: DDDR Comment: With documented pacemaker syndrome—whether it being during ventricular pacing or its functional equivalent (a junctive rhythm with loss of AV synchrony, PVC: with retrograde conduction) it is essential to maintain an appropriate atrio-ventricular contraction sequence [4].

Reference [4]: Barold, S. S., "Cardiac Pacing Hemodynamics: The Pacemaker Syndrome," *Cardio*, 1991; 8: (September) 36–51.

Heldman, D. et al., "True Incidence of Pacemaker Syndrome," *Pace*, 1990; 13: 1742–1750.

Aussbel, U., Furman, S., "The Pacemaker Syndrome, Ann (?) Internal Medicine," 1985; 103: 420–429.

Mode Selection Conclusion 59

1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
None.
11. What is the status of the sinus rhythm (Neuroregulatory abnormality, Normal, Sinus Node dysfunction)?
Sinus Node dysfunction
12. Is AV Block present or is the patient on medications likely to cause AV Block?
Yes.
10. Does Atrial rate increase with physiologic stress?
No.
8. Is there a hypertrophied, non-compliant ventricle?
No.
9. Is there evidence of pacemaker syndrome (fall in blood pressure, retrograde conduction, fall in cardiac output) with ventricular pacing or pre-pacing native rhythm when AV synchrony is lost?
No.
Recommended Mode: DDDR Mode Selection Conclusion 60

1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
None.
11. What is the status of the sinus rhythm (Neuroregulatory abnormality, Normal, Sinus Node dysfunction)?
Sinus Node dysfunction.
12. Is AV Block present or is the patient on medications likely to cause AV Block?
Yes.
10. Does Atrial rate increase with physiologic stress?
Yes.
8. Is there a hypertrophied, non-compliant ventricle?
Yes.
Recommended Mode: DDD Comment Given the hypertrophied, non-compliant ventricle, one wants to maintain AV synchrony as much as possible when the atrium is NOT fibrillation. Hence VVI and VVIR are not appropriate in this setting.

Mode Selection Conclusion 61

1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
None.
11. What is the status of the sinus rhythm (Neuroregulatory abnormality, Normal, Sinus Node dysfunction)?
Sinus Node dysfunction.
12. Is AV Block present or is the patient on medications likely to cause AV Block?
Yes.
10. Does Atrial rate increase with physiologic stress?
Yes.
8. Is there a hypertrophied, non-compliant ventricle?
No.
9. Is there evidence of pacemaker syndrome (fall in blood pressure, retrograde conduction, fall in cardiac output) with ventricular pacing or pre-pacing native rhythm when AV synchrony is lost?
Yes.
Recommended Mode: DDD Comment: With documented pacemaker syndrome—whether it being during ventricular pacing or its functional equivalent (a junctive rhythm with loss of AV synchrony, PVC: with retrograde conduction) it is essential to maintain an appropriate atrio-ventricular contraction sequence [4].

Reference [4]: Barold, S. S., "Cardiac Pacing Hemodynamics: The Pacemaker Syndrome," *Cardio*, 1991; 8: (September) 36–51.

Heldman, D. et al., "True Incidence of Pacemaker Syndrome," *Pace*, 1990; 13: 1742–1750.

Aussbel, U., Furman, S., "The Pacemaker Syndrome, Ann (?) Internal Medicine," 1985; 103: 420–429.

Mode Selection Conclusion 62

1. Does the patient need a pacemaker?
Yes.
2. Will the patient's need for a pacemaker be infrequent?
No.
4. Is the patient mentally incompetent, unaware of surroundings, in need of continual nursing care, etc?
No.
5. Is there evidence of Atrial fibrillation (None, Chronic, Intermittent)?
None.
11. What is the status of the sinus rhythm (Neuroregulatory abnormality, Normal, Sinus Node dysfunction)?
Sinus Node dysfunction
12. Is AV Block present or is the patient on medications likely to cause AV Block?
Yes.

10. Does Atrial rate increase with physiologic stress?
Yes.

8. Is there a hypertrophied, non-compliant ventricle?
No.

9. Is there evidence of pacemaker syndrome (fall in blood pressure, retrograde conduction, fall in cardiac output) with ventricular pacing or pre-pacing native rhythm when AV synchrony is lost?
No.

Recommended Mode: DDD Alternate: DDDR

Comment: While base rate pacing is all that is required at the time of implantation, progression of sinus or AV nodal conduction disease due to intrinsic pathologic processes or medications may render the patient chronotropically incompetent in the future. Rate modulated capability will allow for management of all options.

What is claimed is:

1. A decision support system for providing guidance in programming an implantable cardiac stimulating device, the decision support system interactively coupled to the implantable cardiac stimulating device for interactive use by an operator, comprising:

a storage unit containing at least one decision rule set defining rules for deriving operating parameters for one or more types of implantable cardiac stimulating devices;

rule engine means for selecting, from said plurality of rule sets, a rule set corresponding to a type of implantable cardiac stimulating device being programmed, and for conducting an interactive session with an operator, defined in accordance with said rules of said selected rule set through which programming information is acquired, the programming information being used by said rule engine means to determine an appropriate operating condition for said implantable cardiac stimulating device; and input and output means for enabling said rule engine means to acquire said programming information during said interactive session and for displaying said operating condition determined by said rule engine means.

2. The decision support system of claim 1 further comprising a patient/device database storage means for storing medical information pertaining to patients and to said plurality of types of implantable cardiac stimulating devices.

3. The decision support system of claim 2, including means for providing access by said rule engine means to said patient/device database and to thereby use said medical information to select said rule set corresponding to said type of implantable cardiac stimulating device being programmed.

4. The decision support system of claim 2, including means for storing said rule sets in said patient/device database storage unit.

5. The decision support system of claim 1 further comprising means for providing to the input and output means citations to medical literature which support said operating condition determined by said rule engine means.

6. The decision support system of claim 5, wherein input and output means includes means for displays such citations.

7. The decision support system of claim 1, wherein said rule engine means comprises a microprocessor.

8. The decision support system of claim 1, wherein said storage means stores said rule sets as decision trees.

9. The decision support system of claim 1, wherein said storage means stores said rule sets as deduction-oriented, antecedent-consequent rules.

10. The decision support system of claim 1, wherein said input/output means comprises a device selected from the group consisting of a keyboard, a touch-sensitive screen, and a screen with a light pen to enable said rule engine to acquire said programming information.

11. The decision support system of claim 1, wherein said input/output means comprises a device selected from the group consisting of a display monitor, a printer, and a touch-sensitive screen to enable said rule engine to present said operating condition.

12. A method for providing decision support in programming an implantable cardiac stimulating device, utilizing a decision support system interactively coupled to the implantable cardiac stimulation device for interactive use by an operator, the support system including a storage unit containing at least one decision rule set defining rules for deriving operating parameters for one or more types of implantable cardiac stimulating devices, comprising the steps of:

obtaining medical information pertaining to a patient, and to a type of implantable cardiac stimulating device being programmed;

selecting a rule set, corresponding to said type of implantable cardiac stimulating device being programmed, from a plurality of rule sets stored in the storage unit;

conducting an interactive session with an operator defined in accordance with rules of said selected rule set for providing programming information;

displaying said programming information; and utilizing said displayed programming information to determine an appropriate operating condition for said implantable cardiac stimulating device being programmed.

13. The method of claim 12, wherein said obtaining step comprises obtaining said medical information, at least partially, from a patient/device database.

14. The method of claim 12 further comprising the step of providing citations to medical literature which support said operating condition.

15. The method of claim 12 further comprising the step of telemetrically programming said implantable cardiac stimulating device being programmed in accordance with said operating condition.

16. An implantable cardiac stimulating device programmer that provides decision support in programming of an implantable cardiac stimulating device, the programmer interactively coupled to the implantable cardiac stimulation device for interactive use by an operator, said programmer comprising:

a storage unit containing one or more rule sets defining rules for deriving operating parameters for at least one type of implantable cardiac stimulating device;

rule engine means for selecting from said rule sets, a rule set corresponding to a type of implantable cardiac stimulating device being programmed, and which conducts an interactive session with an operator defined in accordance with said rules of said selected rule set through which programming information is acquired, the programming information being used by said rule engine unit to determine an appropriate operating condition for said implantable cardiac stimulating device;

input/output means for enabling said rule engine means to acquire said programming information during said interactive session and for presenting said operating condition determined by said rule engine unit; and telemetry means for communicating said operating condition to said implantable cardiac stimulating device.

17. The programmer of claim 16 further comprising a patient/device database for storing medical information pertaining to patients and to said types of implantable cardiac stimulating devices.

18. The programmer of claim 17, including means for providing access by said rule engine means to said patient/device database and to thereby use said medical information to select said rule set corresponding to said type of implantable cardiac stimulating device being programmed.

19. The programmer of claim 17, including means for storing said rule sets in said patient/device database.

20. The programmer of claim 16 further comprising means for providing citations to medical literature which support said operating condition determined by said rule engine means.

21. The programmer of claim 16, wherein said input/output means comprises a device selected from the group consisting of a keyboard, a touch sensitive screen, and a screen with a light pen to enable said rule engine means to acquire said programming information.

22. The programmer of claim 16, wherein said input/output means comprises a device selected from the group consisting of a display monitor, printer, and a touch sensitive screen to enable said rule engine to present said operating condition.

* * * * *